(12) United States Patent
Clark

(10) Patent No.: US 9,173,557 B2
(45) Date of Patent: Nov. 3, 2015

(54) METHOD AND APPARATUS THAT FACILITATES DETERMINING REFRACTIVE ERROR

(71) Applicant: Jack Clark, Fresno, CA (US)

(72) Inventor: Jack Clark, Fresno, CA (US)

( * ) Notice: Subject to any disclaimer, the term of this patent is extended or adjusted under 35 U.S.C. 154(b) by 0 days.

(21) Appl. No.: 13/937,105

(22) Filed: Jul. 8, 2013

(65) Prior Publication Data

US 2015/0009475 A1    Jan. 8, 2015

(51) Int. Cl.
*A61B 3/02* (2006.01)
*A61B 3/00* (2006.01)
*A61B 3/032* (2006.01)
*A61B 3/036* (2006.01)

(52) U.S. Cl.
CPC ............... *A61B 3/032* (2013.01); *A61B 3/036* (2013.01)

(58) Field of Classification Search
USPC ................................................. 351/200–246
See application file for complete search history.

(56) References Cited

U.S. PATENT DOCUMENTS

| 2003/0156276 | A1* | 8/2003 | Bowes | 356/124 |
| 2004/0239934 | A1* | 12/2004 | Bowes | 356/400 |
| 2006/0256322 | A1* | 11/2006 | Bowes | 356/124 |

* cited by examiner

*Primary Examiner* — Mohammed Hasan
(74) *Attorney, Agent, or Firm* — Daniel S. Castro; Loza & Loza, LLP

(57) ABSTRACT

Aspects are disclosed for determining refractive error. In an aspect, a line pattern is displayed to a user, and a distance between the line pattern and the user is ascertained. The line pattern includes a first and second line in which an aspect of the line pattern is varied, and where refractive error is quantified based on the distance and a selected variance of the line pattern. In another aspect, the varied aspect of the line is at least one of a width between the first and second line, a thickness of the first or second line, a darkness of the first line or the second line, or a color of the first line or the second line. An input corresponding to a focused line pattern variance selected by the user is then received, and a refractive error is quantified based on the input and an approximate distance between the line pattern and the user.

17 Claims, 16 Drawing Sheets

FIG. 9 Astigmatism target t2, t3, t4 (from left to right), measure at 14.5" from the screen t1, measure at 14.5" from the screen T5 hyperopic thermometer Hyperopic thermometers (H1, H2, H3, H4, measure from 14.5 inches from the screen)

FIG. 15
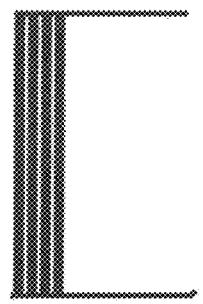
Horizontal and vertical myopic targets Inflexion point target

METHOD AND APPARATUS THAT FACILITATES DETERMINING REFRACTIVE ERROR

TECHNICAL FIELD

The subject disclosure generally relates to eyeglass prescriptions, and more specifically to a mechanism that objectively quantifies refractive error.

BACKGROUND

By way of background concerning conventional refraction mechanisms, it is noted that such mechanisms are often subjective, wherein such subjectivity creates an undesirable variance between calculations performed by different eye care professionals. Furthermore, because many people live in remote areas, the accessibility of those people to eye care professionals is often quite limited. Accordingly, it would be desirable to provide an objective refraction mechanism which is readily accessible to the public. To this end, it should be noted that the above-described deficiencies are merely intended to provide an overview of some of the problems of conventional systems, and are not intended to be exhaustive. Other problems with the state of the art and corresponding benefits of some of the various non-limiting embodiments may become further apparent upon review of the following detailed description.

SUMMARY

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of this summary is to present some concepts related to some exemplary non-limiting embodiments in a simplified form as a prelude to the more detailed description of the various embodiments that follow.

In accordance with one or more embodiments and corresponding disclosure, various non-limiting aspects are described in connection with determining refractive error. In one such aspect, a method is provided, which includes displaying a line pattern to a user, and ascertaining a distance between the line pattern and the user. The line pattern includes a first line and a second line in which the method further comprises varying an aspect of the line pattern. For this particular embodiment, the aspect varied is at least one of a width between the first line and the second line, a thickness of the first line or the second line, a darkness of the first line or the second line, or a color of the first line or the second line. A refractive error is then quantified based on the distance and a selected variance of the line pattern, wherein the selected variance corresponds to a particular aspect variance of the line pattern identified by the user.

In another aspect, a computer-readable storage medium is provided. The computer-readable storage medium comprises a memory component configured to store computer-readable instructions that include instructions for performing various acts. For this particular embodiment, the acts include displaying a line pattern to a user, and varying an aspect of the line pattern. The line pattern includes a first line and a second line, wherein the aspect being varies is at least one of a width between the first line and the second line, a thickness of the first line or the second line, a darkness of the first line or the second line, or a color of the first line or the second line. The acts further comprise receiving an input corresponding to a focused line pattern variance selected by the user, and quantifying a refractive error based on the input and an approximate distance between the line pattern and the user. Here, the input identifies a particular line pattern aspect combination associated with the focused line pattern variance.

In a further aspect, another method is provided, which includes receiving user data associated with a viewing of a line pattern comprising a first line and a second line. Within such embodiment, the user data identifies parameters associated with the line pattern and a distance between the line pattern and the user, wherein the parameters include at least one of a width between the first line and the second line, a thickness of the first line or the second line, a darkness of the first line or the second line, or a color of the first line or the second line. The method then further comprises determining a refractive error based on the parameters associated with the line pattern and the distance between the line pattern and the user.

Other embodiments and various non-limiting examples, scenarios, and implementations are described in more detail below.

BRIEF DESCRIPTION OF THE DRAWINGS

Various non-limiting embodiments are further described with reference to the accompanying drawings in which:

FIG. 15 illustrates exemplary horizontal and vertical myopic targets according to an embodiment.

DETAILED DESCRIPTION

Figure 1:
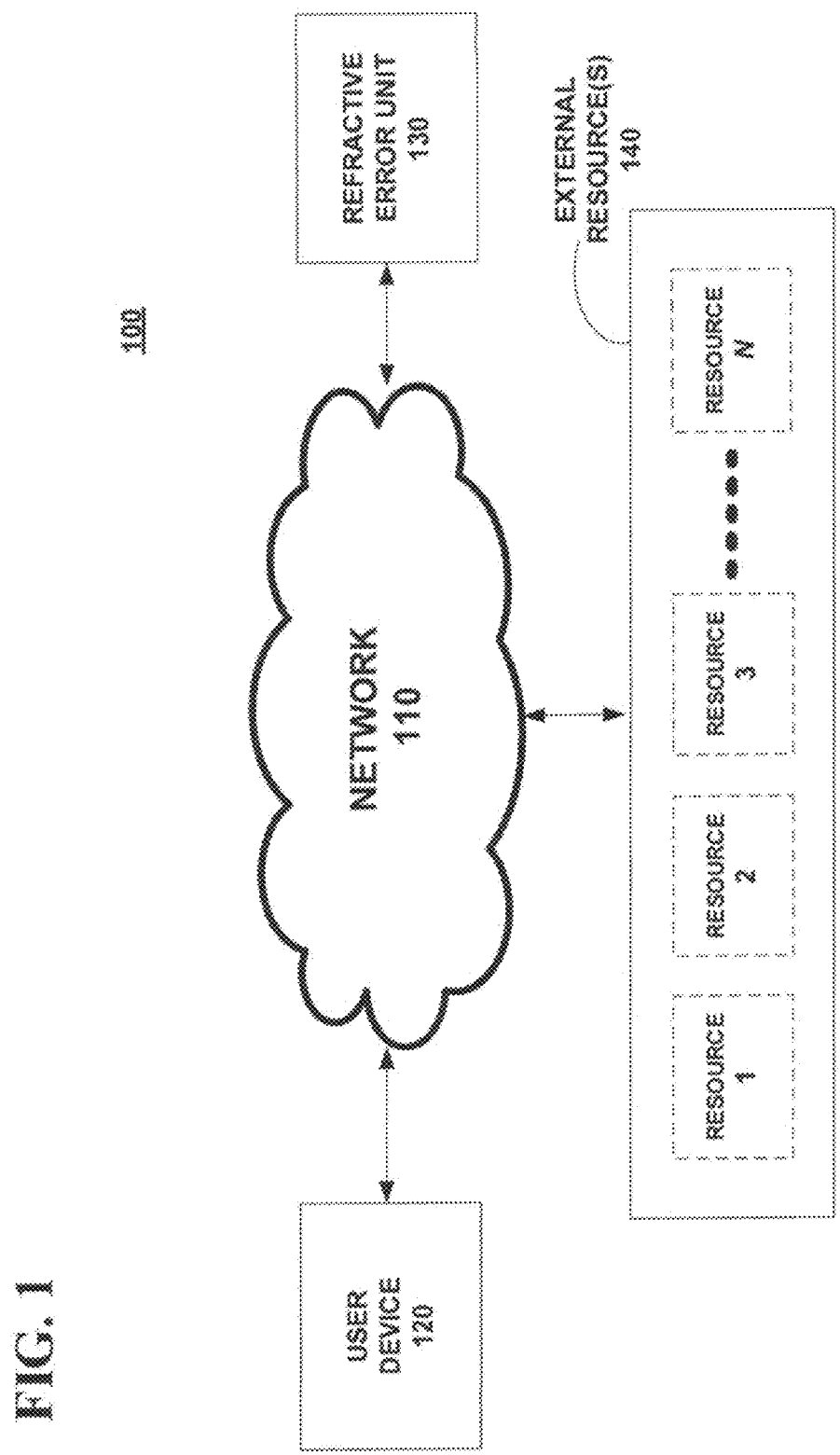
FIG. 1 illustrates an exemplary environment that facilitates ascertaining refractive error in accordance with an aspect of the subject specification.

As discussed in the background, it is desirable to provide a tool in which refractive error is objectively and efficiently ascertained. In particular, it would be desirable to provide a mechanism which allows users to determine their own refractive error, regardless of whether such users are in remote locations. The various embodiments disclosed herein are directed towards such mechanisms.

In an aspect, ascertaining refractive error via direct measurements is contemplated. Indeed, since the divergence power of an eye increases as the eye gets closer to an image (e.g., an image displayed on a smartphone, tablet, laptop, etc.), refractive error can be derived from knowing the distance between the eye and the image once the user observes a particular endpoint. This derived refractive error can then be added to a baseline refractive error to ascertain an actual refractive error. Moreover, because people themselves can measure the distance between their eyes and a screen once a displayed image or other end points appear clear to the user, as subsequently described in the exemplary instructions (e.g., comparing the relative darkness between two lines that are perpendicular to each other to determine the user's astigmatism power). The aspects disclosed herein thus provide a tool for user's to derive their own refractive error from such direct measurements (after adjustments).

To facilitate ascertaining direct measurements more efficiently, aspects for determining such measurements via automated methods are also disclosed. For instance, because the apparatus for displaying the aforementioned image may be equipped with a camera (i.e., a smartphone, tablet, laptop, etc.), it is contemplated that measurements can be extrapolated from self photos taken by the user. Indeed, by comparing a self photo at a known distance, or a self photo with a known measurement that can be standardized (e.g., a self photo with a ruler or tape measure on the user's forehead), to another self photo at a new unknown distance between the user and the screen (i.e., once the displayed image appears clear), this new distance can be readily determined by calculating a relative minification of objects between the two photos. Namely, because of this minification effect, objects in a first self photo taken at a first distance will appear to be smaller in a second self photo taken at a further distance. Rather than taking actual measurements, users may thus simply be instructed to take self photos, which are then compared by a computing device to automatically determine a distance between the user and the screen once the endpoint has been identified. This distance can then be used determine the user's refractive error.

In a further aspect, methods are disclosed which allow users to ascertain their refractive error via indirect measurements. For instance, a method is disclosed which allows users themselves to quantitatively measure the amount of blur a user perceives from an image, wherein the quantitative measurement of such blur corresponds to a particular refractive error. To this end, a technique in which the displayed image is suddenly magnified is also disclosed, which can normalize variability between users. Here, by inducing a sudden magnification of an image (e.g., via a magnification tool on a smartphone) in which the user is allowed to focus on a particular endpoint, and then suddenly eliminating the magnification (i.e., returning the image to its normal size), the immediate effects that the user perceives on the previously focused on endpoint can be used to control for variability in readings (i.e., improve accuracy of the quantified blur). Namely, magnification of an image induces a relaxation of accommodation in the user's eye, which allows for a more accurate reading when the magnified image is immediately reduced to the standard sized image.

In FIG. 1, an exemplary environment that facilitates ascertaining refractive error is provided. As illustrated, environment 100 includes user device 120, which is coupled to refractive error unit 130, and external resource(s) 140 via network 110. Here, it should be noted that user device 120 can be any computing device configured to receive an input from a user (e.g., a mobile device, personal computer, etc.), wherein user device 120 and refractive error unit 130 can be distinct entities or integrated into a single device. In one aspect, user device 120 is configured to display line patterns to a user, wherein user responses to such line patterns are collected and provided to refractive error unit 130. For instance, in an exemplary embodiment, user device 120 is configured to display astigmatism targets and collect various responses regarding how such targets appear to the user (e.g., blurriness, darkness, etc.). Within such embodiment, refractive error unit 130 is configured to calculate/categorize refractive error based in part on these responses. To this end, it should be appreciated that refractive error unit 130 may be further configured to calculate/categorize refractive error based on data retrieved from external resource(s) 140. For instance, external resource(s) 140 may include a medical records database, wherein refractive error unit 130 may be configured to retrieve archived data from such database pertinent to calculating/categorizing refractive error (e.g., age, gender, etc.). Once calculated, it is contemplated that the categorized/calculated refractive error can be sent to other external resource(s) 140 for further use. For example, where external resource(s) 140 is an optometrist, an eyeglass prescription can be readily provided/filled according to the refractive error ascertained by refractive error unit 130.

Figure 2:
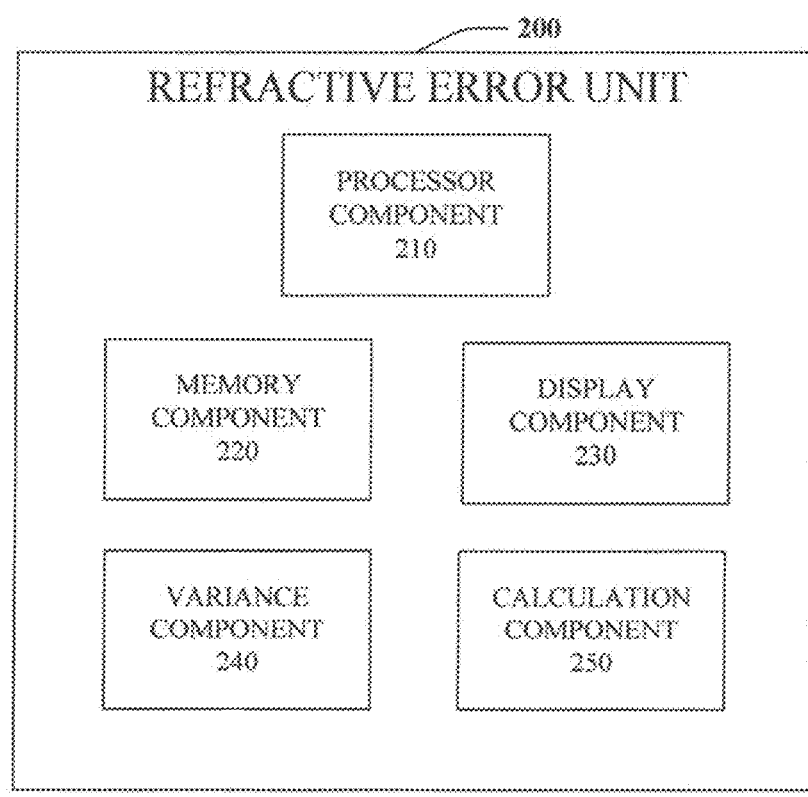
FIG. 2 illustrates a block diagram of an exemplary refractive error unit that facilitates ascertaining refractive error in accordance with an aspect of the subject specification.

Referring next to FIG. 2, a block diagram of an exemplary refractive error unit that facilitates determining a refractive error according to an embodiment is illustrated. As shown, refractive error unit 200 may include processor component 210, memory component 220, display component 230, variance component 240, and calculation component 250. Here, it should be noted that processor component 210, memory component 220, display component 230, variance component 240, and/or calculation component 250 can reside together in a single location or separated in different locations in various combinations including, for example, a configuration in which any of the aforementioned components reside in a cloud. For instance, with reference to FIG. 1, it is contemplated that these components may reside, alone or in combination, in either of user device 120, refractive error unit 130, and/or external resources 140.

In one aspect, processor component 210 is configured to execute computer-readable instructions related to performing any of a plurality of functions. Processor component 210 can be a single processor or a plurality of processors which analyze and/or generate information utilized by memory component 220, display component 230, variance component 240, and/or calculation component 250. Additionally or alternatively, processor component 210 may be configured to control one or more components of refractive error unit 200.

In another aspect, memory component 220 is coupled to processor component 210 and configured to store computer-readable instructions executed by processor component 210. Memory component 220 may also be configured to store any of a plurality of other types of data including data generated by any of display component 230, variance component 240, and/or calculation component 250. Memory component 220 can be configured in a number of different configurations, including as random access memory, battery-backed memory, Solid State memory, hard disk, magnetic tape, etc. Various features can also be implemented upon memory component 220, such as compression and automatic back up (e.g., use of a Redundant Array of Independent Drives configuration). In one aspect, the memory may be located on a network, such as a "cloud storage" solution.

As illustrated, refractive error unit 200 may further comprise display component 230 and variance component 240. Within such embodiment, display component 230 is configured to display a line pattern having a first and second line to a user, whereas variance component 240 is configured to vary an aspect of the line pattern. Here, any of a plurality of variances is contemplated including, for example, a width between the first line and the second line, a thickness of the first line or the second line, or a darkness of the first line or the second line. Furthermore, although the varying of the line pattern may be controlled by refractive error unit 200, it is also contemplated that the varying may be controlled via a user calibration of the line pattern (e.g., user calibration via user device 120).

In another aspect, refractive error unit 200 also comprises calculation component 250, which is configured to quantify a refractive error based on an input received from the user and an approximate distance between the displayed line pattern and the user. Within such embodiment, the user input corresponds to a focused line pattern variance selected by the user, wherein the input identifies a particular line pattern aspect combination associated with the focused line pattern variance. To this end, it should be appreciated that calculation component 250 may be configured to quantify a refractive error in any of a plurality of ways. For instance, calculation component 250 may be configured to access a lookup table, wherein the lookup table associates a particular refractive error value to each of a plurality of line pattern aspect combinations.

Calculation component 250 may also, however, be configured to quantify a refractive error by extrapolating data from an image received from the user. For example, in an embodiment where the user input further comprises an image of the user contemporaneous to the displaying, calculation component 250 may be configured to quantify a refractive error by extrapolating the approximate distance of the user from the image. Here, the extrapolating can be performed in various ways. For instance, the extrapolating may comprise extrapolating the approximate distance based on an approximate arm length. In another aspect, however, the extrapolating may comprise comparing the image to a reference image of the user. In yet another aspect, the extrapolating may comprise extrapolating the approximate distance based on measured dimensions of a reference object within the image (e.g., a ruler).

A refractive error may also be calculated via use of astigmatism targets. For instance, display component 230 may be configured to display an astigmatism target, wherein calculation component 250 may be configured to quantify a refractive error by determining an astigmatism axis. Within such embodiment, the astigmatism target may include an astigmatism axis wheel comprising a plurality of arc lines, wherein the determining of the astigmatism axis is based on a particular arc line selected by the user. Alternatively, the determining of the astigmatism axis may be based on compass data received from a user device.

Figure 3:
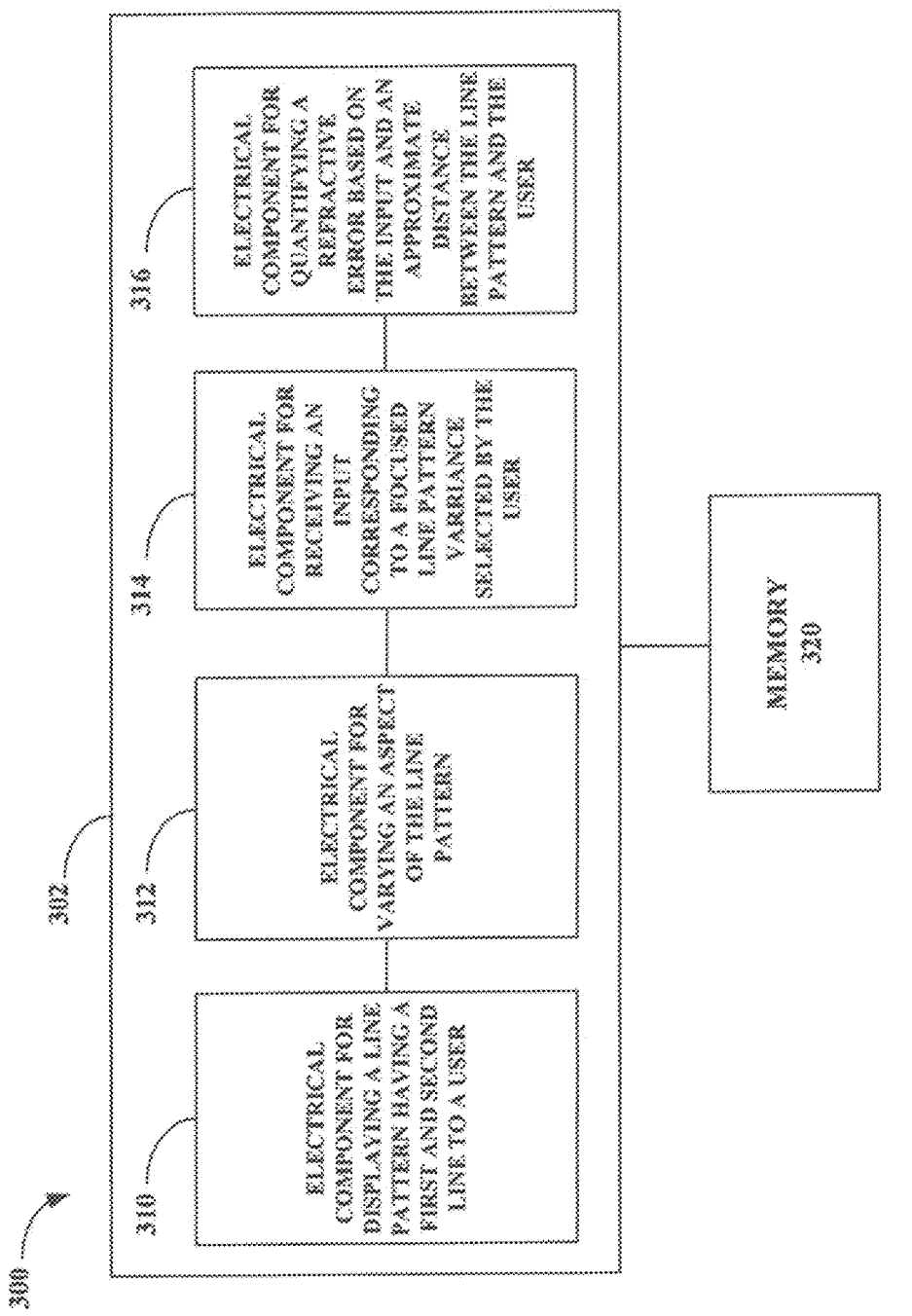
FIG. 3 illustrates a first exemplary coupling of electrical components that effectuate ascertaining refractive error according to an embodiment.

Turning to FIG. 3, illustrated is a system 300 that facilitates determining a refractive error according to an embodiment. System 300 and/or instructions for implementing system 300 can reside within a computing device, for example (e.g., within refractive error unit 130). As depicted, system 300 includes functional blocks that can represent functions implemented by a processor using instructions and/or data from a computer readable storage medium. System 300 includes a logical grouping 302 of electrical components that can act in conjunction. As illustrated, logical grouping 302 can include an electrical component for displaying a line pattern having a first and second line to a user 310, as well as an electrical component for varying an aspect of the line pattern 312. Logical grouping 302 can also include an electrical component for receiving an input corresponding to a focused line pattern variance selected by the user 314. Further, logical grouping 302 can include an electrical component for quantifying a refractive error based on the input and an approximate distance between the line pattern and the user 316. Additionally, system 300 can include a memory 320 that retains instructions for executing functions associated with electrical components 310, 312, 314, and 316. While shown as being external to memory 320, it is to be understood that electrical components 310, 312, 314, and 316 can exist within memory 320.

Figure 4:
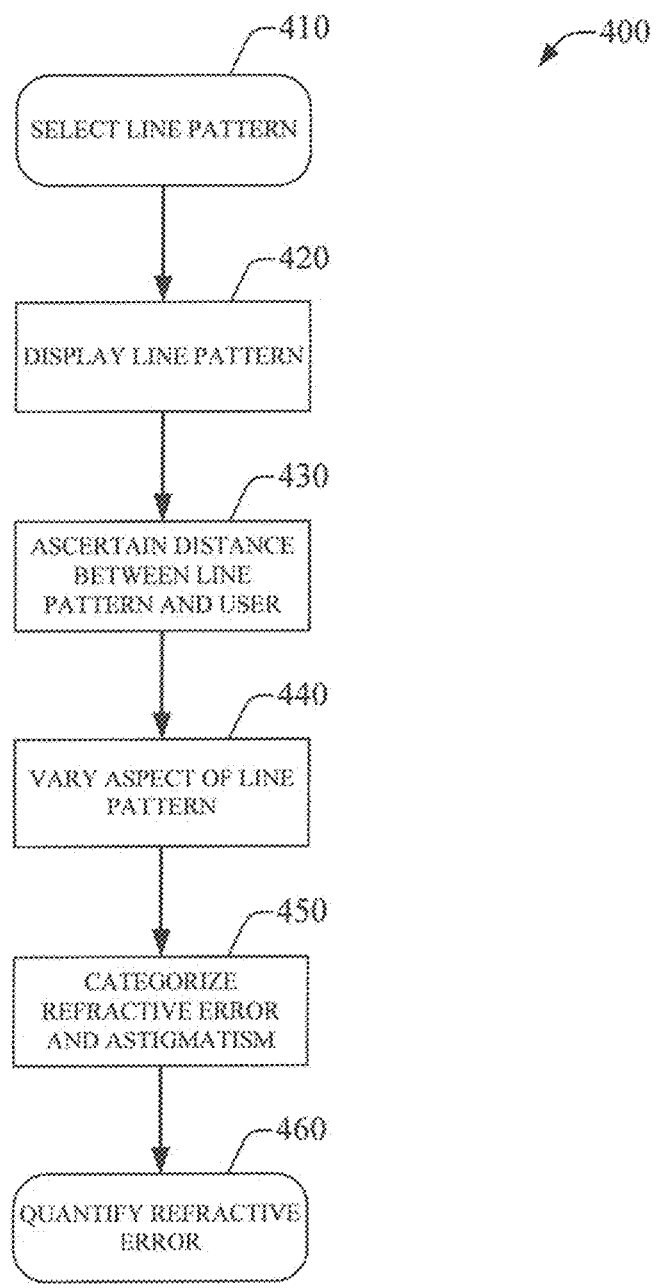
FIG. 4 is a flow diagram of a first exemplary methodology that facilitates ascertaining refractive error in accordance with an aspect of the subject specification.

Referring next to FIG. 4, a flow chart illustrating an exemplary method that facilitates ascertaining refractive error is provided. As illustrated, process 400 includes a series of acts that may be performed within a computer system (e.g., refractive error unit 200) according to an aspect of the subject specification. For instance, process 400 may be implemented by employing a processor to execute computer executable instructions stored on a computer readable storage medium to implement the series of acts. In another embodiment, a computer-readable storage medium comprising code for causing at least one computer to implement the acts of process 400 is contemplated.

As illustrated, process 400 begins with a line pattern being selected at act 410 and subsequently displayed at act 420. Within such embodiment, it should be appreciated that any of a plurality of line patterns may be displayed in which the line pattern has at least a first and second line. For instance, an astigmatism target may be displayed, wherein the astigmatism target may include an astigmatism axis wheel comprising a plurality of arc lines.

After the line pattern is displayed, a distance between the line pattern and the user is ascertained at act 430. An aspect of the line pattern is then varied at act 440, wherein the aspect is at least one of a width between the first line and the second line, a thickness of the first line or the second line, or a darkness of the first line or the second line. The particular refractive error and astigmatism can then be categorized at act 450, wherein the refractive error is subsequently quantified at act 460.

Here, it should be appreciated that the categorizing and quantifying respectively performed at acts 450 and 460 are based on data collected from the user. In a particular aspect, refractive error is quantified based on the distance and a selected variance of the displayed line pattern, wherein the selected variance corresponds to a particular aspect variance of the line pattern identified by the user. Refractive error may also be quantified by accessing a lookup table, however, wherein the lookup table associates a particular refractive error value to each of a plurality of line pattern aspect combinations. In a further aspect, the quantifying comprising quantifying at least one of a myopic refractive error or a hyperopic refractive error.

The quantifying may also, however, comprise quantifying at least one of a myopic astigmatism refractive error or a hyperopic astigmatism refractive error, if an astigmatism target is displayed. Within such embodiment, the quantifying of the at least one of the myopic astigmatism refractive error or the hyperopic astigmatism refractive error may further comprise determining an astigmatism axis, wherein the determining of the astigmatism axis is based on a particular arc line selected by the user. The quantifying may also comprise quantifying a mixed astigmatism refractive error.

Figure 5:
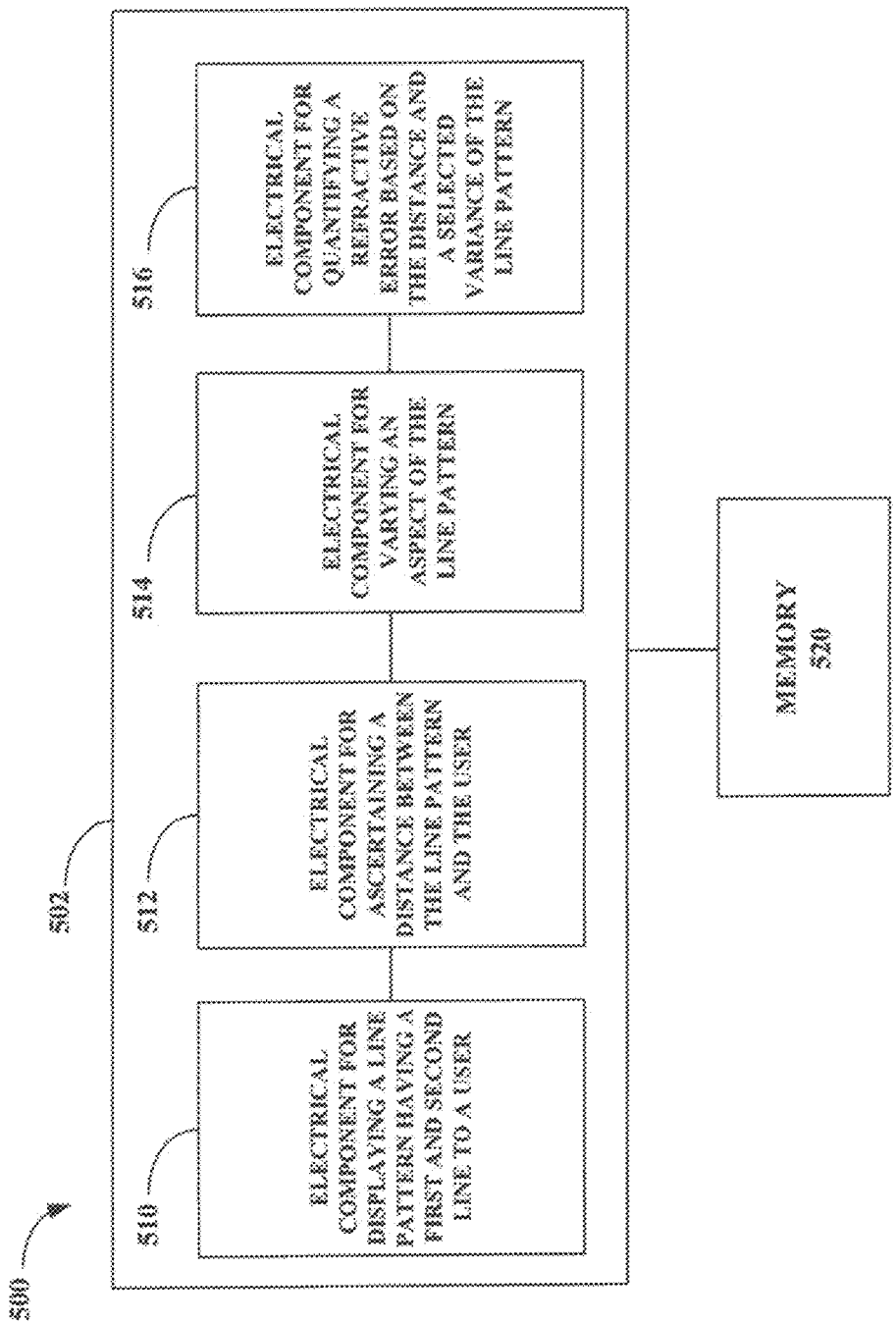
FIG. 5 illustrates a second exemplary coupling of electrical components that effectuate ascertaining refractive error according to an embodiment.

Turning to FIG. 5, illustrated is a system 500 that facilitates determining a refractive error according to an embodiment. Similar to system 300, system 500 and/or instructions for implementing system 500 can reside within a computing device, for example (e.g., within refractive error unit 130). As depicted, system 500 includes functional blocks that can represent functions implemented by a processor using instructions and/or data from a computer readable storage medium. System 500 includes a logical grouping 502 of electrical components that can act in conjunction. As illustrated, logical grouping 502 can include an electrical component for displaying a line pattern having a first and second line to a user 510, as well as an electrical component for ascertaining a distance between the line pattern and the user 512. Logical grouping 502 can also include an electrical component for varying an aspect of the line pattern 514. Further, logical grouping 502 can include an electrical component for quantifying a refractive error based on the distance and a selected variance of the line pattern 516. Additionally, system 500 can include a memory 520 that retains instructions for executing functions associated with electrical components 510, 512, 514, and 516. While shown as being external to memory 520, it is to be understood that electrical components 510, 512, 514, and 516 can exist within memory 520.

Figure 6:
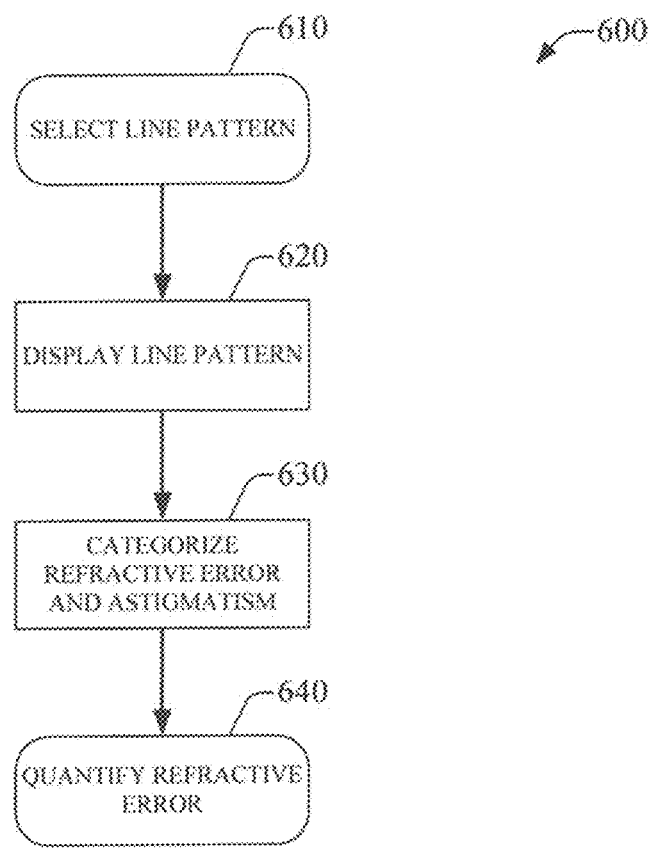
FIG. 6 is a flow diagram of a second exemplary methodology that facilitates ascertaining refractive error in accordance with an aspect of the subject specification.

Referring next to FIG. 6, a flow chart illustrating an exemplary method that facilitates ascertaining refractive error is provided. As illustrated, process 600 includes a series of acts that may be performed within a computer system (e.g., refractive error unit 200) according to an aspect of the subject specification. For instance, process 600 may be implemented by employing a processor to execute computer executable instructions stored on a computer readable storage medium to implement the series of acts. In another embodiment, a computer-readable storage medium comprising code for causing at least one computer to implement the acts of process 600 is contemplated.

As illustrated, process 600 begins with a line pattern being selected at act 610 and subsequently displayed at act 620. Within such embodiment, it should be appreciated that any of a plurality of line patterns may be displayed in which the line pattern has at least a first and second line. For instance, an astigmatism target may be displayed, wherein the astigmatism target may include an astigmatism axis wheel comprising a plurality of arc lines.

After the line pattern is displayed, a particular refractive error and astigmatism is categorized at act 630, wherein the refractive error is subsequently quantified at act 640. Here, it should be appreciated that the categorizing and quantifying respectively performed at acts 630 and 640 are based on data collected from the user. In a particular aspect, refractive error is determined based on the parameters associated with the displayed line pattern and a distance between the line pattern and the user. Within such embodiment, such parameters include at least one of a width between the first line and the second line, a thickness of the first line or the second line, a darkness of the first line or the second line, or a color of the first line or the second line. Refractive error may also be determined by accessing a lookup table, however, wherein the lookup table associates a particular refractive error value to each of a plurality of line pattern aspect combinations.

Exemplary Networked and Distributed Environments

One of ordinary skill in the art can appreciate that various embodiments for implementing the use of a computing device and related embodiments described herein can be implemented in connection with any computer or other client or server device, which can be deployed as part of a computer network or in a distributed computing environment, and can be connected to any kind of data store. Moreover, one of ordinary skill in the art will appreciate that such embodiments can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Figure 7:
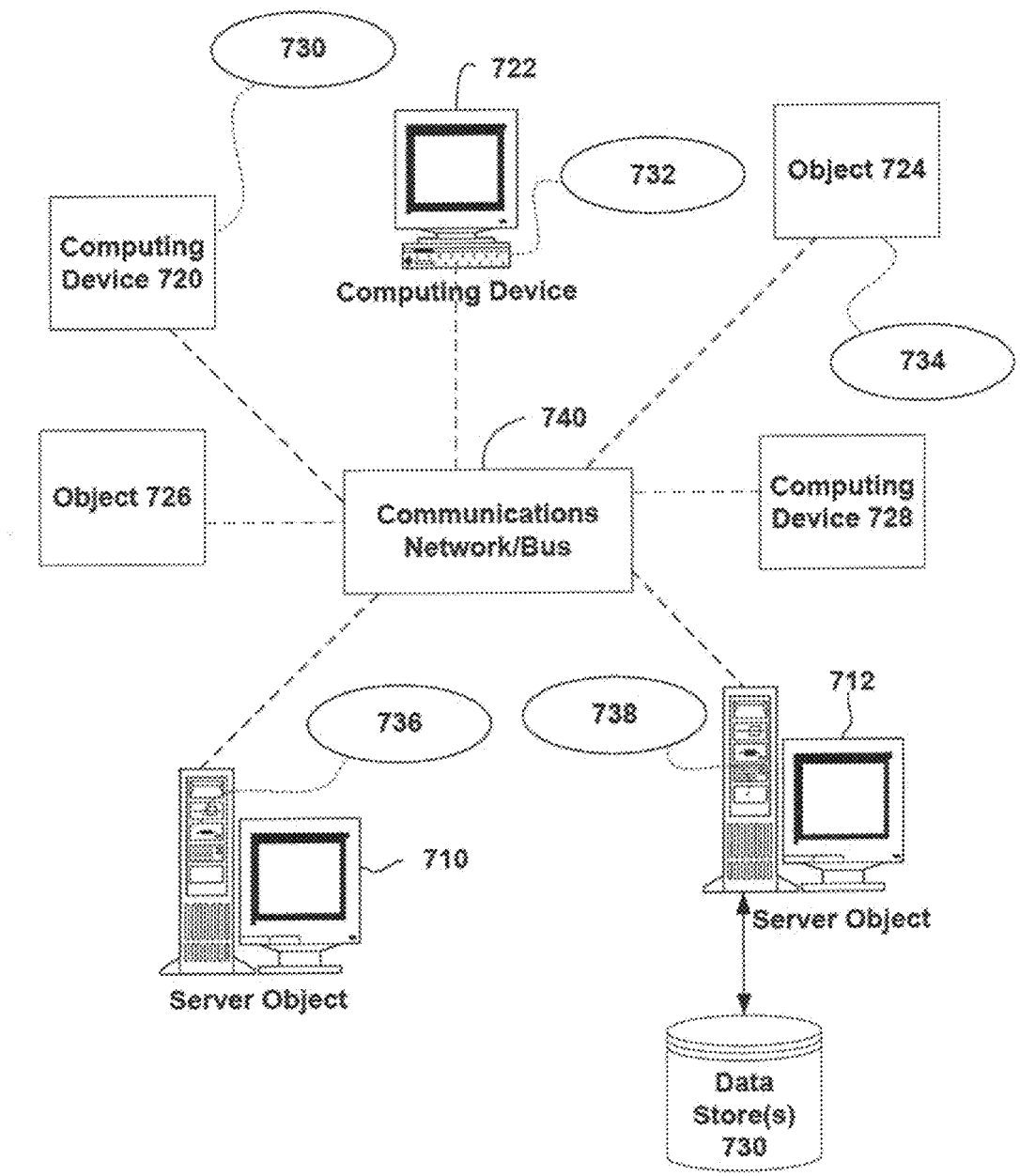
FIG. 7 is a block diagram representing exemplary non-limiting networked environments in which various embodiments described herein can be implemented.

FIG. 7 provides a non-limiting schematic diagram of an exemplary networked or distributed computing environment. The distributed computing environment comprises computing objects or devices 710, 712, etc. and computing objects or devices 720, 722, 724, 726, 728, etc., which may include programs, methods, data stores, programmable logic, etc., as represented by applications 730, 732, 734, 736, 738. It can be appreciated that computing objects or devices 710, 712, etc. and computing objects or devices 720, 722, 724, 726, 728, etc. may comprise different devices, such as PDAs (personal digital assistants), audio/video devices, mobile phones, MP3 players, laptops, etc.

Each computing object or device 710, 712, etc. and computing objects or devices 720, 722, 724, 726, 728, etc. can communicate with one or more other computing objects or devices 710, 712, etc. and computing objects or devices 720, 722, 724, 726, 728, etc. by way of the communications network 740, either directly or indirectly. Even though illustrated as a single element in FIG. 7, network 740 may comprise other computing objects and computing devices that provide services to the system of FIG. 7, and/or may represent multiple interconnected networks, which are not shown. Each computing object or device 710, 712, etc. or 720, 722, 724, 726, 728, etc. can also contain an application, such as applications 730, 732, 734, 736, 738, that might make use of an API (application programming interface), or other object, software, firmware and/or hardware, suitable for communication with or implementation of various embodiments.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for exemplary communications made incident to the techniques as described in various embodiments.

Thus, a host of network topologies and network infrastructures, such as client/server, peer-to-peer, or hybrid architectures, can be utilized. In a client/server architecture, particularly a networked system, a client is usually a computer that accesses shared network resources provided by another computer, e.g., a server. In the illustration of FIG. 7, as a non-limiting example, computing objects or devices 720, 722, 724, 726, 728, etc. can be thought of as clients and computing objects or devices 710, 712, etc. can be thought of as servers where computing objects or devices 710, 712, etc. provide data services, such as receiving data from computing objects or devices 720, 722, 724, 726, 728, etc., storing of data, processing of data, transmitting data to computing objects or devices 720, 722, 724, 726, 728, etc., although any computer can be considered a client, a server, or both, depending on the circumstances. Any of these computing devices may be processing data, or requesting services or tasks that may implicate various embodiments and related techniques as described herein.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the user profiling can be provided standalone, or distributed across multiple computing devices or objects.

In a network environment in which the communications network/bus 740 is the Internet, for example, the computing objects or devices 710, 712, etc. can be Web servers with which the computing objects or devices 720, 722, 724, 726, 728, etc. communicate via any of a number of known protocols, such as HTTP. As mentioned, computing objects or devices 710, 712, etc. may also serve as computing objects or devices 720, 722, 724, 726, 728, etc., or vice versa, as may be characteristic of a distributed computing environment.

Exemplary Computing Device

As mentioned, several of the aforementioned embodiments apply to any device wherein it may be desirable to utilize a computing device according to the aspects disclosed herein. It is understood, therefore, that handheld, portable and other computing devices and computing objects of all kinds are contemplated for use in connection with the various embodiments described herein. Accordingly, the below general purpose remote computer described below in FIG. 8 is but one example, and the embodiments of the subject disclosure may be implemented with any client having network/bus interoperability and interaction.

Although not required, any of the embodiments can partly be implemented via an operating system, for use by a developer of services for a device or object, and/or included within application software that operates in connection with the operable component(s). Software may be described in the general context of computer executable instructions, such as program modules, being executed by one or more computers, such as client workstations, servers or other devices. Those skilled in the art will appreciate that network interactions may be practiced with a variety of computer system configurations and protocols.

Figure 8:
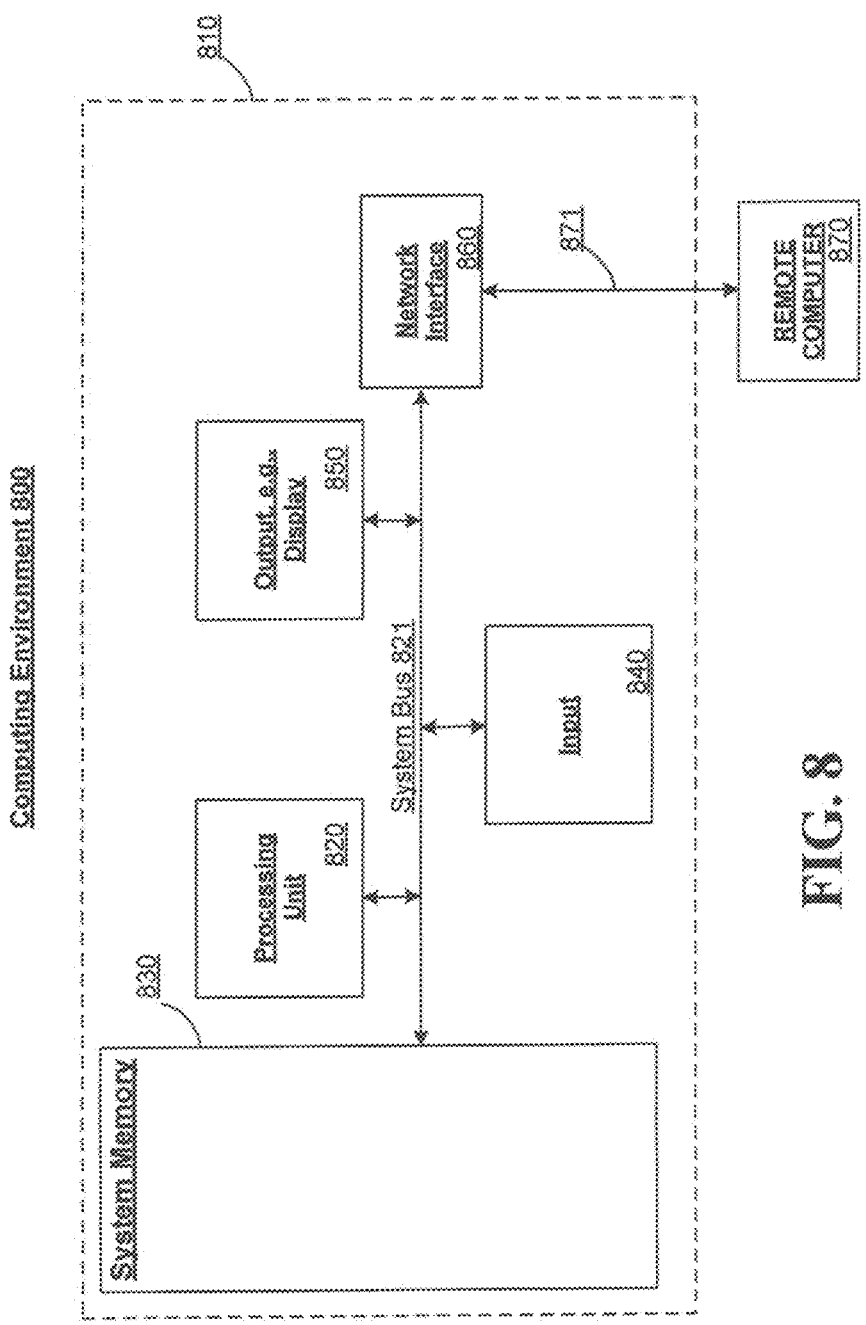
FIG. 8 is a block diagram representing an exemplary non-limiting computing system or operating environment in which one or more aspects of various embodiments described herein can be implemented.

FIG. 8 thus illustrates an example of a suitable computing system environment 800 in which one or more of the embodiments may be implemented, although as made clear above, the computing system environment 800 is only one example of a suitable computing environment and is not intended to suggest any limitation as to the scope of use or functionality of any of the embodiments. The computing environment 800 is not to be interpreted as having any dependency or requirement relating to any one or combination of components illustrated in the exemplary operating environment 800.

With reference to FIG. 8, an exemplary remote device for implementing one or more embodiments herein can include a general purpose computing device in the form of a handheld computer 810. Components of handheld computer 810 may include, but are not limited to, a processing unit 820, a system memory 830, and a system bus 821 that couples various system components including the system memory to the processing unit 820.

Computer 810 typically includes a variety of computer readable media and can be any available media that can be accessed by computer 810. The system memory 830 may include computer storage media in the form of volatile and/or nonvolatile memory such as read only memory (ROM) and/or random access memory (RAM). By way of example, and not limitation, memory 830 may also include an operating system, application programs, other program modules, and program data.

A user may enter commands and information into the computer 810 through input devices 840 A monitor or other type of display device is also connected to the system bus 821 via an interface, such as output interface 850. In addition to a monitor, computers may also include other peripheral output devices such as speakers and a printer, which may be connected through output interface 850.

The computer 810 may operate in a networked or distributed environment using logical connections to one or more other remote computers, such as remote computer 870. The remote computer 870 may be a personal computer, a server, a router, a network PC, a peer device or other common network node, or any other remote media consumption or transmission device, and may include any or all of the elements described above relative to the computer 810. The logical connections depicted in FIG. 8 include a network 871, such local area network (LAN) or a wide area network (WAN), but may also include other networks/buses. Such networking environments are commonplace in homes, offices, enterprise-wide computer networks, intranets and the Internet.

As mentioned above, while exemplary embodiments have been described in connection with various computing devices and networks, the underlying concepts may be applied to any network system and any computing device or system in which it is desirable to publish, build applications for or consume data in connection with the aspects described herein.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but generally known by those of skill in the art.

In view of the exemplary systems described supra, methodologies that may be implemented in accordance with the disclosed subject matter can be appreciated with reference to the various figures. While for purposes of simplicity of explanation, some of the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

While in some embodiments, a client side perspective may be inferred, it is to be understood for the avoidance of doubt that a corresponding server perspective exists, or vice versa. Similarly, where a method is practiced, a corresponding device can be provided having storage and at least one processor configured to practice that method via one or more components.

While the various embodiments have been described in connection with the embodiments of the various figures, it is to be understood that other similar embodiments may be used or modifications and additions may be made to the described embodiment for performing the same function without deviating there from. Still further, one or more aspects of the above described embodiments may be implemented in or across a plurality of processing chips or devices, and storage may similarly be affected across a plurality of devices. Therefore, the present invention should not be limited to any single embodiment, but rather should be construed in breadth and scope in accordance with the appended claims.

Figure 9:
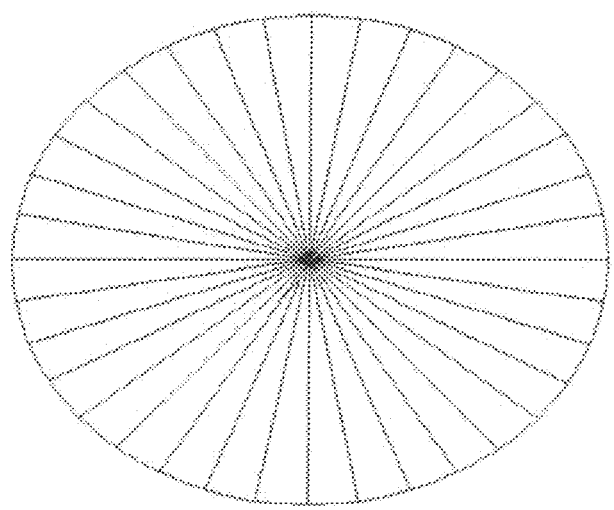
FIG. 9 illustrates an exemplary astigmatism target according to an embodiment.

Exemplary Self Refraction Instructions
Instructions for Online Refraction Using a Smartphone:
First, enter the identifying data or information required below; carefully read and follow the directions for measurements; and remember to write down or enter your measurements where required. With careful measurements this technique for obtaining glasses prescriptions can be more accurate than subjective refractions at the eye doctor's office.
Identifying data:
 Name _ _
 Age _ years old Date of birth _
 E mail Address _
We will start by having you look at the astigmatism target illustrated in FIG. 9. First we will determine if you are farsighted (or presbyopic) or nearsighted. Place the phone on a flat surface (chair or a table), now while looking at the astigmatism target from a standing position, gradually approach the phone, noticing if the lines; or a line on the target along one axis (pointing in a certain direction) at least, become clearer or more focused as you get closer to the image; but only at a certain distance, or a range that might be only a few inches; and then gets blurrier or less focused as you keep moving towards the phone. This means you are probably nearsighted, or if only one line becomes in focus, at least one of your refractive axes is nearsighted. Also, notice as you get closer to the phone and the original line that became in focus now starts to blur, if another line ninety degrees from the original line becomes the darkest line on the astigmatism target, while the original line becomes the lightest and most out of focus line. This means you are nearsighted and have astigmatism. The last line that becomes in focus as you move closer to the screen is the spherical axis line. The first line that became in focus is the astigmatism axis line. Later, we will measure the refractive power at the spherical axis line and the astigmatism axis line to determine your glasses prescription. If the lines become more distinguishable as you get closer, but never become in sharp focus, this usually indicates that you are farsighted. If also, one line along one axis (pointing in one direction) remains the darkest or more in focus when compared to all the other lines, over a wide range of distances (several feet) from the phone this usually means you may be farsighted and have astigmatism also. The darkest line is the spherical axis line. If the lines are all pretty clear, you may have a smaller refractive error and may need to place the phone on the floor or propped up on a table at a greater distance from you to determine whether the lines are becoming clearer at some point as you get closer to the image. It is ok if, as you keep moving closer, the image begins to blur again.

Check the Box that Best Describes Your Experience:
1._ nearsighted (the lines at least on one axis get clearer as I move towards the target), the images are clearer at near and blurry at distance.
2._ farsighted (the lines are blurry at distance but don't ever become clear at near either, as I move closer to the target)
3._ presbyopia (getting older, must be over forty) the lines are clear at a distance but get blurrier as I move closer to the target.

Next, we would like to determine if you have astigmatism. If while moving closer to the visual target you notice that a line is becoming darker or more focused than the rest at one axis (along one direction) often with the lines immediately next to that line also becoming more in focus also, with relatively larger white spaces around the lines, then you have an astigmatism. Also notice as you continue getting closer to the image if a new line at ninety degrees from that original line becomes darker with larger spaces around it, while the original line becomes lighter and more blurry; this means you have nearsighted astigmatism (the new line being your spherical axis line).

In mixed astigmatism you will notice as you approach the image, your spherical axis line will become dark and in focus over several inches because you are nearsighted at that axis, but the line ninety degrees from it (your astigmatism axis line) although may be easier to see the closer you get will never become clear or in focus, often will remain shorter with narrower and greyer white spaces around it, because you are farsighted at that axis (astigmatism axis line). It is ok if the astigmatism axis line is darker at distances far away from the screen initially (this can occur if the farsighted refractive error is less than the nearsighted refractive error), but as you get closer and recognize the spherical axis line, becoming the darkest line, in sharp focus over several inches and then start to fade as you continue to get closer to the screen, the astigmatism axis line (ninety degrees from the spherical axis line) will never become darker or in focus.

If you have farsighted astigmatism, as you approach from far away from the screen to closer, the image will become easier to see but never clear, or in focus; usually only one line will be darker at one axis (along one direction), your spherical axis line, with wider white spaces around it and it will remain the darkest line (for weak astigmatism you may only notice the relatively larger whiter spaces along one direction or at one axis, and not notice that one line appears darker).

Check the Box that Best Matches Your Experience:

1a._ nearsighted astigmatism (with two axes—the second one ninety degrees from the original, closer to the visual target, representing the spherical axis with plus cylinder).

1b._ nearsighted with mixed astigmatism (only one axis, only lines along one axis remain dark and eventually become in focus over several inches, and do NOT fade and get replaced by a line ninety degrees from the original line as you move closer to the target)

1c._ nearsighted without significant astigmatism (no line is darker than the others, all the white spaces are about the same size)

2a._ farsighted astigmatism (all lines remain out of focus as I move closer to the image, but one line is darker with larger white spaces around it)

2b._ farsighted without significant astigmatism (the lines get easier to see the closer I get to the phone but never become in sharp focus, no line is darker than the rest (or switches from one to another) and the white spaces separating the lines are about the same size)

3._ presbyopia (the lines are clear at a distance but become blurrier as I get closer to the phone, all the lines are about the same in darkness and have about the same size spaces around them)

We have determined whether you are farsighted or nearsighted, and whether you have a significant astigmatism or not. If you have astigmatism we will next need to define your astigmatism axis in degrees. If you are nearsighted, this axis is always determined at the distance from your phone, where the line along the astigmatism axis first becomes in focus. (Again, the astigmatism axis line is the FIRST line you encounter, that becomes dark or in focus as you are approaching the image). If you are farsighted, we need to define your spherical axis in degrees, and can determine your astigmatism axis in degrees as well, since it is almost always located ninety degrees from your spherical axis. For farsighted clients the spherical axis line is the line that appears darker or more in focus than all the other lines. For nearsighted clients, likewise, we can determine your spherical axis in degrees from your astigmatism axis in degrees that you have already measured for us.

(1a, 1b, or 2a) Often just by looking at the astigmatism target, with the top of your phone pointing along the ninety degree axis, you can determine your astigmatism axis directly from the scale on the astigmatism target by noting the degrees that the darkest line points to. You can use magnified sections of the scale below to help you in your reading. If you have two astigmatism axes (nearsighted astigmatism, 1a) we need to know the axis in degrees at the furthest distance from the phone (the astigmatism axis line) as you move from out to in or towards the phone, and the second line that becomes in focus (ninety degrees from the first line) or nearest to the screen (the spherical axis line). Measure your axis in degrees from the scale just outside the circle that the darkest line is pointing to at the distance from the phone where the line is at its widest or darkest, for both the spherical axis line and the astigmatism axis line.

Spherical axis 1 _, Astigmatism axis 2 _:

Alternatively, you can use the compass technique described below or astigmatism wheels to determine your astigmatism axis if these techniques are easier for you.

(Skip this section if you have already determined your astigmatism axis in degrees)

Compass Technique:

Place your phone on a flat surface, turn on compass (under utilities) on your smartphone, and orient your phone, and yourself, to face due north (approximately zero degrees). While moving your head slowly towards the astigmatism target from above, from out to in, if you can, start far enough away from your phone that all the lines appear blurry, moving towards the phone until you first get a dark line which is darker than all the other lines surrounded by relatively larger spaces around it, orient your phone so the top of the phone is pointing directly in line with that first dark line; then, switch to compass and write down the degrees or enter below (Astigmatism axis line). This is your astigmatism axis for 1a (enter your data under axis 2), and your spherical axis for 1b, 2a (enter your data for axis 1). If you marked 1a above, myopic astigmatism, then keep moving closer to the target looking at the axis line ninety degrees or at a right angle from the astigmatism axis line. This is your spherical axis (arbitrary name). When this line becomes the darkest line on the astigmatism target, again rotate your phone so it is pointing directly in line with your spherical axis, where the lines on both sides of the darkest line are equal in darkness. Switch to compass function and enter the degrees for your spherical axis (axis 1). If your refractive error is too mild to easily perform the measurements you can use the astigmatism axis wheels below to obtain the same measurements.

(Skip this next section if you have already determined your spherical and astigmatism axis in degrees)

Figure 10:
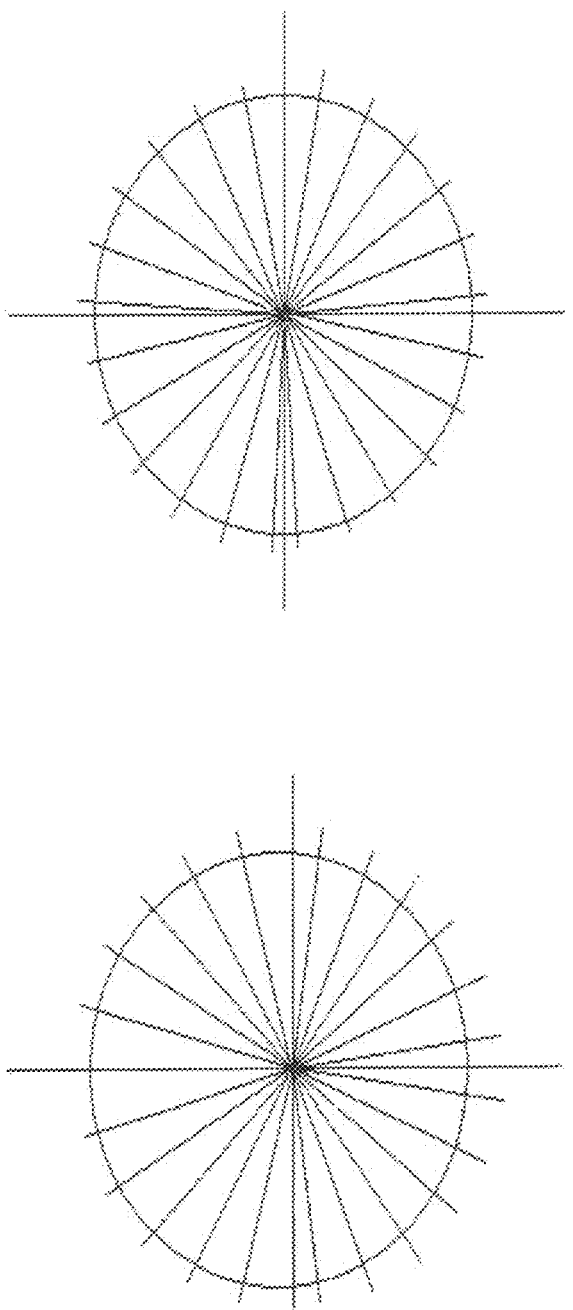
FIG. 10 illustrates exemplary astigmatism axis wheels according to an embodiment.

(Astigmatism Axis Wheels). Astigmatism axis wheels, as illustrated in FIG. 10, can be used to determine your astigmatism axis, wherein you are asked to look at astigmatism targets and identify the line that is darkest on each target. Begin far away from the target where all the lines may appear blurry and move slowly towards the targets until you first identify one line that is darker than the rest or appears to have wider white spaces around it. At that distance identify the line that is darkest on each target.

Figure 12:
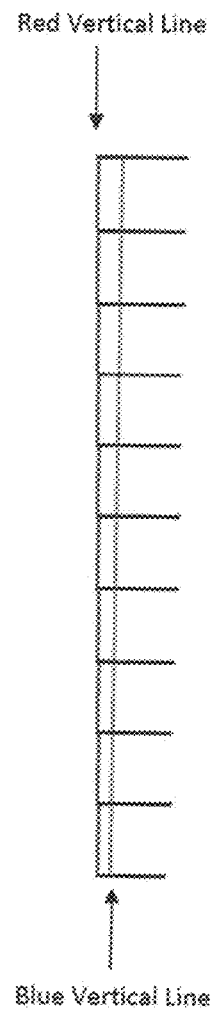
FIG. 12 illustrates an exemplary T1 thermometer according to an embodiment.
Figure 13:
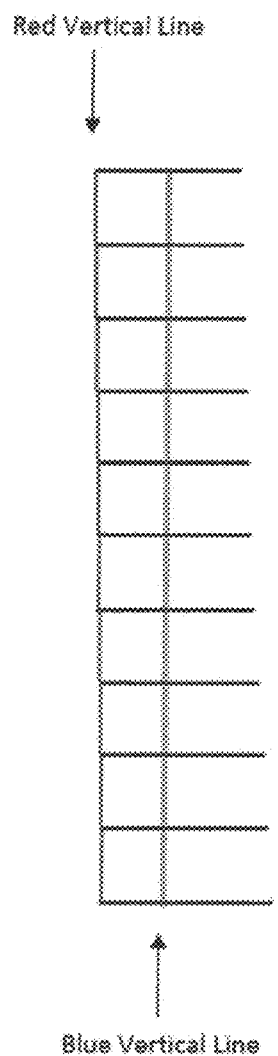
FIG. 13 illustrates an exemplary T5 thermometer according to an embodiment.
Figure 14:
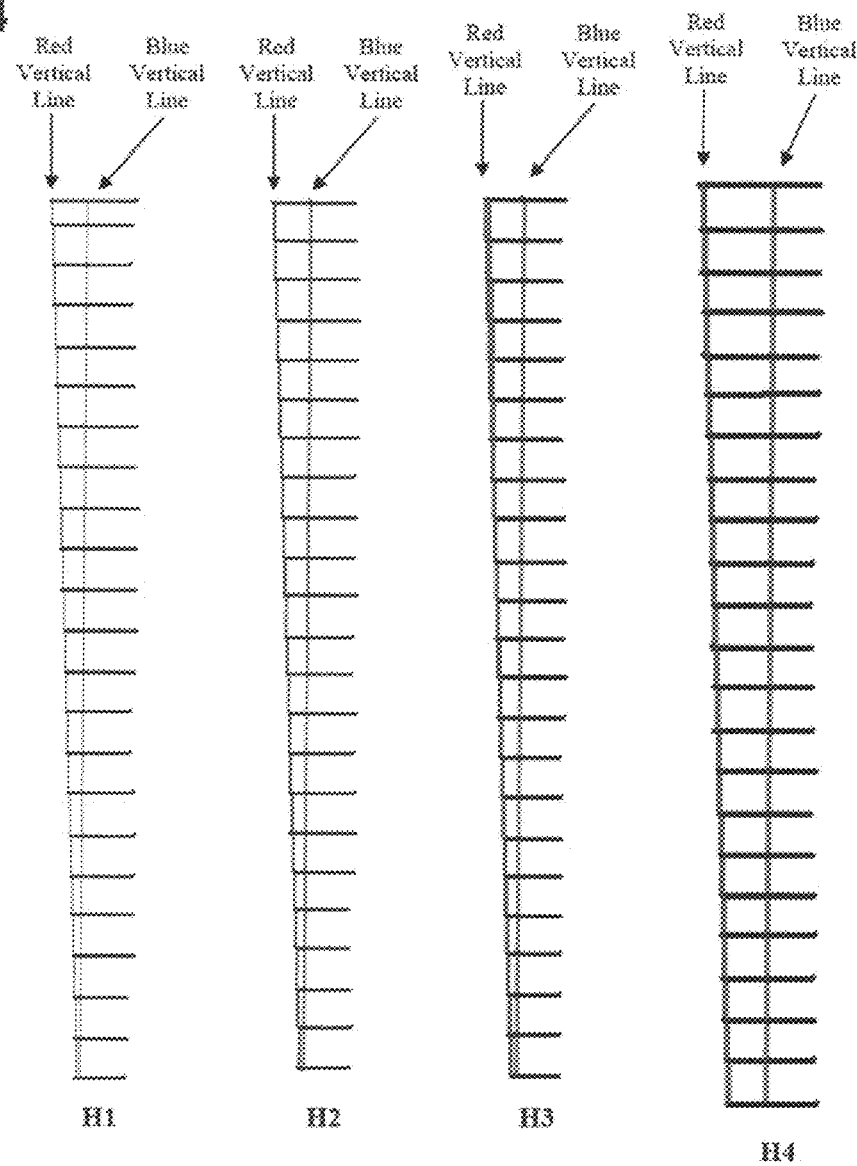
FIG. 14 illustrates exemplary hyperopic thermometers according to an embodiment.

Next we will determine an estimate of the refractive power of your spherical and astigmatism axes. If you have farsighted refractive error you will be using the Clark™ hyperopic thermometers h1, h2, h3, h4 illustrated in FIG. 14 to find your refractive error and the t1, t2, t3, t4, or t5 thermometers illustrated in FIGS. 11-13 to confirm your end point. If you have nearsighted refractive error you will be using the horizontal and vertical myopic targets and will be asked to confirm your measurements with either a second set of thermometers, myopic thermometers t1, t2, t3, t4 or t5; or obtain an inflexion point measurement to determine your astigmatism power to improve accuracy of your measurements. Clients over forty have an option to use astigmatism target measurements also. If you have nearsighted with mixed astigmatism refractive error you will be using the same above visual targets just mentioned to measure your nearsighted spherical axis, and the H and T thermometers to measure your farsighted astigmatism axis measurements. On the thermometers as a rule, if you see the white space or halo just inside the blue line (left eye being tested), or the central whitish space (the white space separating the red and blue lines and their blurs) is beveled up towards the blue line, it means you are probably farsighted at that axis; if it's just inside the red lines, and the central whitish space is beveled up towards the red line, you are probably nearsighted at that axis. It is inverted for the right eye being tested. As always we measure only one eye at a time, with the other eye closed or covered, and obtain two measurements within an eighth of an inch apart when measuring the distance that end points occur from your eye to the screen, or the same reading on a thermometer twice in a row to confirm the measurements. Remember that making careful accurate measurements will lead to more accurate glasses for you, and in the end, better sight for you as well. This technique in the end just allows you to quantitatively measure your own blur from your own refractive error. Excepting physical problems with the eye, the amount of blur you have is directly related to the amount of refractive error you have, which allows us to determine your glasses or contact lenses prescription from your answers. (In other words it is all on you to provide us with accurate measurements and information, but we will do our best to guide you).

Hyperopic Measurements

T Thermometers:

Instructions for measuring t-thermometers: T thermometers can be used for measuring farsightedness, and farsighted astigmatism, and mixed astigmatism measurements. Vertical T thermometers include a left outside red line and a right inside blue line, with black horizontal lines separating the thermometer into ten segments, with the narrowest segment at the bottom of the thermometer and the widest segment at the top. A horizontal thermometer is identical except for lying on its side with the blue line now on top and the red line at the bottom, the widest segment is now the outside segment on the right, and the narrowest segment is the last segment on the left hand side.

Methods for Measurements (with Definitions and Descriptions):

(instructions are for left eye measurements, the same instructions can be used for the right eye measurements except since the hyperopic blur originates from outside lines and moves towards the nose side, (fovea slightly tilted toward the ear) dependent on which eye is being tested with pull and release maneuvers, every blue line is changed to red line, and upper right hand corner is changed to upper left hand corner when appropriate). In other words the true white space we are measuring is located just inside the blue line for left eye vertical measurements, and just inside the red line for vertical right eye measurements. For hyperopic refractive errors the true white space is located just inside the line on the nose side of the eye being tested, for myopic measurements the true white space is located just inside of the line on the ear side of the eye being tested.

(Easier to follow if you perform the maneuvers on the t-thermometers while you read)

1. Ten second pull and release: When measuring a segment on a vertical thermometer, first place two of your fingers on the phone's screen each horizontally just outside of the segment you are measuring (so the segment is inside your fingers), now spread your fingers along the screen to maximally magnify the segment or spread the lines apart. When measuring on a horizontal thermometer place your fingers above and below the segment you are measuring to spread the segment apart, or to maximally magnify the segment, while you will be attempting to identify the true white space just inside the blue line. The true white space is a separation, where the blurs off the blue and red lines are far enough apart that they don't overlap, and allow the background white space of the phone screen to come through as a horizontal space just inside the blue line. Maintain your focus on the grey blur just inside the true white space to allow it to become brighter and more well defined during the ten second pause, or if it is not present, where you expect it to emerge. Count to ten under your breath, or possibly longer until the true white space becomes well defined and very bright (should be the same brightness as the white background space above, outside the segment). Then suddenly release your fingers from the screen while focusing on the true white space to see if it persists just at the edge of the grey blur, just inside the blue line. It should still be just as bright as the white background space just above and outside the thermometer as if it was an extension of the white background space into the segment. Care must be taken to distinguish the true white space from the secondary white space. A secondary white space can form in any segment containing the central whitish grey space, or a completely hazy segment. It is located just inside the blue line, is noticeably duller than the true white space, and remains the exact same width as you follow it from one segment to the next along the thermometer. The central whitish-grey space is easily recognized as a whitish-grey space separating the blurry outside red and inside blue lines, appearing widest inside the widest segment, and appearing to bevel up towards the blue line as you focus on narrower and narrower segments down the thermometer, as the central whitish grey space becomes narrower as well. A secondary white space occurs in the exact same location just inside the blue line as the true white space, and usually emerges just after the true white space disappears when the segment contracts or shortly after. A secondary white space will always appear to be slightly greyer, and not quite as bright as the true white space. The easiest way to distinguish a secondary white space from a true white space is once they are settled after the initial contraction, re-spread the segment apart again focusing on the white space; as you magnify the segment again, by pulling the segment apart with your fingers on the screen; a secondary white space will disappear and get replaced by a much brighter true white space, a true white space when re-magnified will not change in brightness, just appear to get wider or move up a little bit, you will never lose your fixation as you focus on it as you pull and release the segment. Often five quick pull and release maneuvers in a row immediately following a ten second pull and release can cause the secondary white space to disappear and get replaced with the homogeneous grey blur extending all the way to the blue line following the release and the contraction back to normal size, where as the true white space most easily seen by focusing on it at the upper right hand corner of the segment next to the next widest segment on the thermometer, will persist throughout the maneuvers and be still present at the end of the maneuvers. On a hazy space segment, during the release maneuver you will always lose fixation on the true white space for a split second before the secondary white space emerges (appears to flip over it). When the grey blur extends all the way to the blue line after the contraction that segment is easily defined as a hazy space segment.

2. Independent five quick pull and release technique, method already described above only this time five pull and release maneuvers in a row, allows the eye focus to fatigue and makes it easier to define the hazy space segments, as often secondary white space can be made to disappear. The method is performed at a slow but continuous pace, it is only called quick because you don't pause ten second before releasing the magnification, although it is consecutive the next pull and release maneuver must be paused enough to see if the white space disappears in between the pull and release maneuvers. It is used as an independent method for accurately confirming the first white space segment and the first hazy space segment. Often after estimates have directed you to within three segments of your end point on a particular thermometer (the end point being identifying the first hazy space segment or the first white space segment); these two critical segments have characteristically different responses to a five quick pull and release maneuver. When the maneuver is performed on the first white space segment, while focusing on just the white space just inside of the blue line, and comparing the white space's appearance when the segment is pulled apart or magnified, to its appearance when the segment is released and allowed to contract back to its original size; in the magnified state the white space appears as a wider separation, equal in brightness to the background white space on the phone screen, as the segment is released your eye usually never loses its fixation on the white space, as it becomes much thinner in the contracted state, but stays at the same level of brightness. As the procedure is repeated it usually gets wider and thinner, or appears to move slightly up and down, but persists throughout the maneuvers, and is present when the maneuvers conclude. This is in contrast to the first hazy space segment, where in its magnified state the white space appears equally bright as the background white space on the screen, but when it is released the bright white space is replaced by a noticeably duller secondary white space, or after multiple maneuvers may even disappear in the contracted state just after the release, only to immediately reappear or noticeably brighten with the next spread apart portion of the maneuver, fixation on the white space is usually broken for a split second as the secondary white space sort of flips over the true white space and replaces it in the contracted state immediately following the release, if it is still present. By noting these differences during the maneuvers when testing the segments side by side, one can determine the first hazy space segment and count backwards down the thermometer (as the segments get narrower) to determine the total number of hazy space segments for your reading.

3. Twenty second gaze, with your eye relaxed just gaze at the background white space beside the thermometer while counting to twenty to yourself under your breath before directing your attention to the thermometer you are going to measure, this relaxes your focus or accommodation which allows the true white spaces on the wider segments and also the central purple and grey lines on the narrower segments to emerge and become more defined. Used in obtaining baseline measurements for vertical and horizontal thermometers.

4. (One, two punch) A ten second pull and release maneuver followed by a single quick pull and release maneuver at the end, can allow you to determine between hazy space segments and white space segment by seeing if after the second quick pull and release the white space persist or is closed out by the grey blur going all the way the blue line when viewing the space just under the blue line in the center of the segment. This time the second pull and release is a very quick re-magnification and sudden release as an emphasis, just to see if the grey blur can close completely to the blue line.

Figure 11:
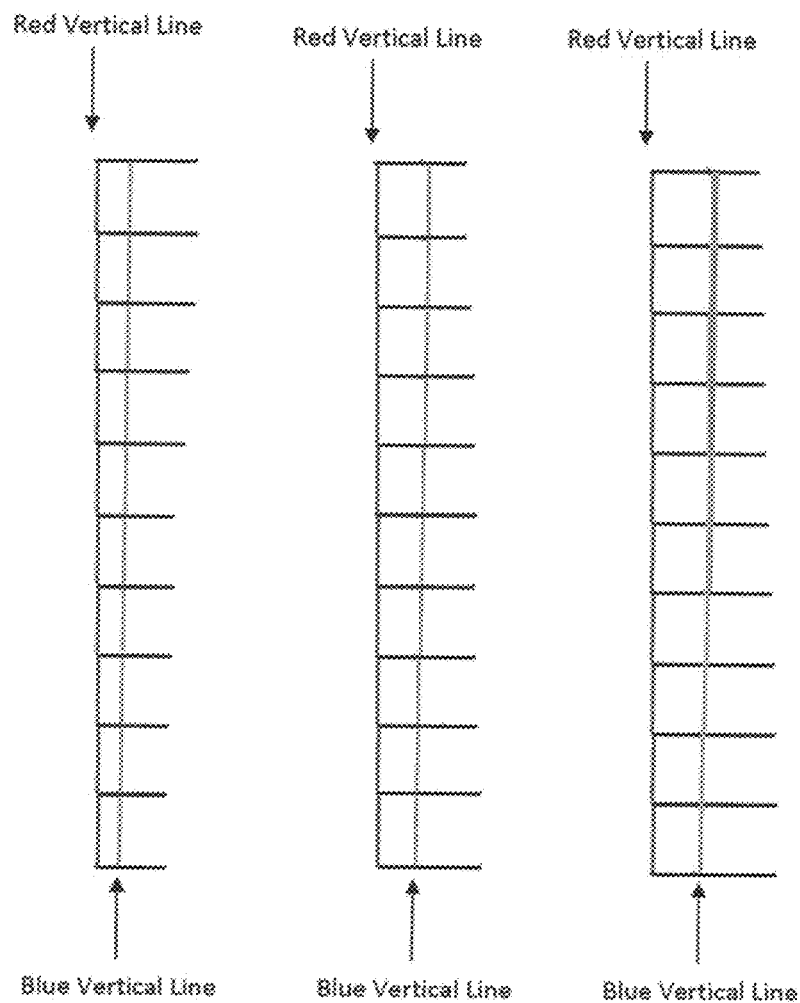
FIG. 11 illustrates exemplary T-thermometers according to an embodiment.

Directions:

Activating the t– Thermometer:

First at 14.5" from the phone's screen, find T2, T3, T4 images, as shown in FIG. 11. Align the phone lengthwise along either the spherical axis line (darkest line on the astigmatism target) or the astigmatism axis line (align the phone widthwise along the darkest line on the astigmatism target) that you are measuring. Only the eye you are measuring should be open. Find the widest top segment on the T4 thermometer (the largest thermometer in the series). Each of the thermometers are divided into ten progressively larger segments as you go from the bottom up, the outside borders of the thermometers segment defined by a red line to the left and a blue line to the right. Try and identify the true white space or white halo just inside the blue line on the top segment of the T4. If you can't be sure place two of your fingers on the phone's screen each horizontally just outside of the segment you are measuring (so the segment is inside your fingers), now spread your fingers to maximally magnify the segment or spread the lines apart. This will allow you to easily see and define the true white space (if it is there) just inside the blue line. Next adjust your distance from the phone so the true white space you have just identified is at its brightest, where a small movement away from the screen or a small movement towards the screen seems to make the white space duller, or the faint grey line less apparent which defines its inside border. Make all your t-thermometer readings (vertical and horizontal) form this new distance.

Vertical Thermometer measurements; (For thermometers aligned along their lengthwise axis within thirty degrees of a vertical ninety degree straight up and down line):

Quick Directions:

The end point is any white space inside the blue line, method: count twenty seconds (while focusing on the background white space) to allow white spaces to emerge, (the white space often will be as bright as the background white space). Find the smallest thermometer that appears to contain white spaces just inside the blue line. For t1 and t2 measurements, you are then allowed a single pull and release to make a questionable white space to disappear, after the release, a hazy space will stay hazy, in a white space segment, the white space will remain visible; for t3 measurements you are allowed a ten second pull and release followed by a single quick pull and release, where again after the maneuvers the white space will persist in the white space segments but the blur will close over them in the hazy space segment. If the result is unsure it is always fine to wait a few seconds between your readings and re-measure using the same method. When the end points appear to be on t4 or t5, after your initial search for any white spaces (similar in brightness to the background whitespace) inside the blue lines fails to identify any on t3 or below, then the method switches to a ten second pull and release and the retention of any white space (usually as bright as the background white space) inside the blue line, confirmed by five quick pull and releases. If five pull and release maneuvers make the primary white space disappear then it is a hazy space segment; if while focusing on the white space at the upper right hand corner just inside the blue line and just outside the white region of the center of the segment (which gets considerably narrower as you move up the t5 thermometer), you can maintain fixation on the original true white space through the five maneuvers and it is present at the end of the five maneuvers, then it is a white space segment. At t5 same method: only start from the top of the thermometer and work your way down segment by segment.

Detailed Instructions: (Optional, if Having Difficulty Obtaining an End Point with the Quick Directions)

First, just gaze at the T4 thermometer for twenty seconds to allow your eye to relax, this will allow the central whitish space to emerge, which again is a light grey white space that forms in between the red and blue blurs. It has a characteristic slant or bevel towards the blue line as the central white space progresses downward over narrower segments; you may even notice that it merges into the blue line at some point, if the end point is on T4. The end point is the intersection of the first white space segment and the adjacent (slightly narrower) first hazy space segment. All segments and thermometers below or narrower to the first hazy space segment contain hazy space segments, all segments above or wider than the first white space segment contain white space segments.

If all the segments on t4 contain the central whitish grey space, then move to t3 and again just gaze at the thermometer for twenty seconds to allow the central whitish grey space to emerge. On vertical thermometers usually the last segment that contains the central whitish space before it merges with the blue line is often the first white space segment, the segment below is the first hazy space segment. The first hazy space segment can be confirmed by the maneuver described above where you pull apart the segment or maximally magnify it and then suddenly release it, as it return to its normal size you will notice the red-grey blur snap shut over the white line or separation just inside the blue line if it is a hazy space segment. You are only allowed one quick pull and release to see if you can close out the white space. Likewise this same maneuver on the segment just above it, the first white space segment, you will notice the red blur close more slowly and often incompletely allowing the white halo to still be seen at the edge just inside the blue line. If there is no clearly defined central whitish space on the T3 thermometer, and most of the T4 white space can be made to disappear with a single quick pull and release, then your method switches over to a ten second pull and release, followed by five quick pull and release maneuvers to define the first white space segment, defined by the presence of a true white space that persists through the maneuvers, usually focusing on the space in the upper right hand corner of the segment. With the presence of any central whitish grey space on t3, use the twenty second gaze, with a single quick pull and release to define the first hazy space segment, defined by the widest segment that contains no central whitish grey space. With large refractive errors, secondary white spaces may still be present in the upper segments on the t4 thermometer, but using the ten second pull and release, followed by five quick pull and release maneuvers will usually close out the secondary white spaces identifying them as hazy space segments. These maneuvers are necessary because with very high refractive errors a true white space may not appear even with the pull maneuver maximizing the magnification, so you can't easily determine whether the white space is a true white space or a secondary white space, although it will be noticeably duller than the white background space when compared. Now as you turn to the t5 thermometers for an end point, the true white space may only appear as a white glow in the upper right hand corner that can persist through the ten second pull and release and the five quick pull and release maneuvers, after the segment finishes its contraction back to its original size. With small refractive errors it may appear as a faint, double light grey line just inside the blue line suggesting a white space bordered by the blue line on the outside and a faint light grey line separating it from the red or grey blur on the inside of the segment, that doesn't disappear with a single quick pull and release. On t1 thermometers the presence of any central white space (no matter how thin) counts as a white space segment, as opposed to a light grey center that spreads across the whole segment, and holds through a quick pull and release in hazy space segments.

When measuring the hyperopic axis of a mixed astigmatism refractive error (where your other axis is nearsighted) the last space containing the central whitish beveled line is still often the first white space segment, however it is confirmed by holding the segments spread apart for ten seconds to allow your eye to relax prior to your release to allow you to pick up and identify the true white space and notice that the white halo or space is still just present after the segment contraction ends, or the presents of a double light grey line may be present at the end, both which defines that segment as the first white segment. With mixed astigmatism you have to push the white space segments as far down the thermometer (towards narrower segments) as you can while still being able to confirm the space for greater accuracy. Once you have defined the first white space segment start with that segment and count upward to obtain the total number of white space segments and record that reading and the thermometer that was measured on. (Or if it is easier identify the first hazy space segment and count that space and all the segments under it to obtain the total number of hazy space segments)

Horizontal Measurements: (Defined as an Axis Line within Sixty Degrees of a Perfect One Hundred Eighty Degree Horizontal Line)

Quick Instructions:

Begin with the t1 thermometer and moving upward to determine the number of completely grey segments that do not contain a central white space within the segment after a ten second pull and release maneuver. A secondary dull white space immediately below the blue line after the ten second pull and release doesn't count as a central white space, as long as the red-grey blur appears to extend all the way to the blue line after the release, and the dull white space is exactly the same width as all the segments narrower to it to the left. As soon as it appears wider than the narrower segments to the left, it counts as a central white space. Record your answer (for example, when measuring from the bottom of the thermometer up, if the last completely grey segment (CGS) occurs on the widest segment on t1, record ten CGS on t1. By looking at the scale below, this in turn can help direct you to your end point, which most likely is on in the first few segments on t3).

Now start on t3, and using a ten second pull and release maneuver, followed by a quick pull and release, as a primary means of testing the individual segments on the thermometer, usually starting from either the top down or the bottom up, until you find the end point which is a true white space (may be very thin but clearly visible) just inside the blue line, that persists after a ten second pull and release maneuver, and can be confirmed by not disappearing with, and still being present at the end of, five quick pull and release maneuvers immediately following a ten second pull and release maneuver; as opposed to the slightly narrower segment just beside it (the first hazy space segment) where the grey blur either closes over the white space after the ten second pull and release, (while focusing on the grey blur and then shifting your focus to the white space just before the release) or during the five quick pull and release maneuvers following.

Detailed Directions: (Optional, if Having Difficulty Obtaining and End Point with Quick Instructions)

Horizontal t– thermometer measurements: In measuring horizontal axis lines the end point is always the true white space, a thin, bright, white line just below the blue line, that can first be identified through a ten second pull and release maneuver, and confirmed by five pull and release maneuvers in a row, the first white space identified by being able to focus and fixate on the thin white line or space throughout the maneuvers, where as the first hazy segment immediately to the right of that segment, where the same maneuvers cause the grey whitish blur in the center eventually to close over the white line merging it with the rest of the slightly hazy center of the segment being tested. By the time the end point is on the upper segments of T4, and T5 segments there is only a white halo or glow just inside the blue line, where your ability to fixate on the halo, that is your focus is never broken during the pull and release maneuvers is never lost when examining the first white space segment. The white halo is closed over and eventually merged into the grey haze during the maneuvers in the first hazy segment (next narrower segment) just to the right of the first white space segment.

It's best to repeat the measurements at least twice to confirm you are getting consistent results.

Myopic Reading Utilizing T Thermometers:

Quick Directions:

To begin with, obtain an out to in reading on a horizontal or vertical myopic target, aligned along the spherical or astigmatism axis line you are measuring. Use the results from the directions to direct you to the correct thermometer that should contain your end point.

Here the t thermometers for horizontal reading are viewed with the red line on top, blue line at the bottom; your end point is the presence of a white halo or space just inside the red line or its blur. Your end point for vertical measurements can often be determined by focusing on the background white space for ten seconds to relax your accommodation, then reading the segment on the thermometer where the white space just inside the red line separating the red and blue blurs, ends. If the white space just inside the red line doesn't emerge, maximally magnify the widest segment at the top of the thermometer to identify the white space and then follow it down the thermometer focusing on the white space or the red line to maintain it until it disappears at the first hazy spaced segment, confirmed by a ten second pull and release (focusing on the blue blur while counting to ten) noting the white space disappear at the first hazy space segment but persist at the first white space segment.

Detailed Instructions: (Optional, if Having Difficulty Finding the End Point with the Quick Direction)

A special situation can develop for clients over forty with mild nearsightedness at distance, if the astigmatism target has identified a nearsighted refractive error at the vertical axis, but when viewing the t1 thermometer, while testing the left eye, the white space is located just inside the blue line on T1, instead of just inside the red line, this indicates there is a hyperopic or farsighted end point on t1. This is caused when the presbiopic refractive error adds more farsightedness, at the near distance you are measuring from, than your own nearsightedness at distance can overcome. Your end point now becomes, counting any central white space inside the blue line on t1, because now you are measuring a hyperopic refractive error.

When making your measurements in general, count that segment that you have defined as the first white space segment and the segments above it, or the first hazy space segment and the segments below it, whichever is easier, and on which thermometer (t1, t2, t3, or t4) to record the total number of white space segments, for example eight white space segments on t2.

General Appearance of the Thermometers at 14.5" (to Estimate the Thermometer Containing the End Point)

For end points on specific thermometers (the thermometer that contains the first hazy space and white space segments that are adjacent to each other, all wider segments above containing white space segments and all narrower segments below containing hazy space segments). For t1 vertical myopic measurements the general appearance of the thermometers (t4 through t1) contains a large whitish or bluish, grey space in the center of the segments and relatively well defined or thinner red and blue lines, the larger thermometers (t2, t3, t4) often have a noticeable brighter white halo just inside the red line that you can follow all the way down to the t1 thermometer. For end points on t2 often t4 thermometers look the same relatively well defined red and blue lines with a noticeable white halo equal in brightness to the white background space, most of the segments on the t1 target are grey across the whole segment. The upper segments on t1 and most of the segments on t2 may have a secondary lighter grey white halo just inside the red line on vertical measurements, but the halos are duller than the white background space, and can easily be distinguished from white space segments by a ten second pull and release maneuver. Pulling the segments apart will create a real separation between the blurs, and a true white halo just as bright as the background white space (since that's what it is) and noticeably brighter than false halo which still exists but has moved just to the right of the new true white space or halo. With the release part of the maneuver the bright white space will disappear as the blur closes or snaps shut over the separation as the segment narrows, except in the white space segments where a thin white halo will persist and still match the brightness of the white background. For end points on t3, the segments are completely blurry on t1 and t2, if a false white halo exists it can easily be distinguished from a true halo by a pull and release maneuver, by seeing the true separation or white halo as bright as the background white space appear just inside the red line and watch it disappear with the release. T4 continues to have a bright white halo at the edge of the white space in the center of the segment, which can persist through pull and release maneuvers, usually just at the edge, or just inside the red line where the red line is bordered by the clearer space in the center of the segment. As the end point moves onto the t4 thermometer the center white space separating the upper and lower borders of the individual segments continues to narrow as well, the bright white halo begins to look more like a bright glow just inside the red line just outside of the narrow white space in the center of the segment, you can still determine the end point by ten seconds pull and releases, until the first white space and hazy space segments are identified. Looking at t5 there will still be a white halo or glow all along the left side of the thermometer just inside the red line for end points on t4.

Myopic Horizontal and Vertical Targets, Out to in, to Estimate Refractive Errors at Distance and Predict Correct t Thermometer End Points:

Skip the next two paragraphs if the measurements have already been made under the myopic measurement section, move on to the specific thermometer your measurements have directed you to, and confirm the general appearance description from the above paragraph, to check on consistency. Then if needed proceed to detailed instructions for the particular t-thermometer you have been directed to below.

To begin with use the horizontal myopic target or vertical myopic target aligned with the spherical axis line and/or the astigmatism axis line you have identified on the astigmatism target above (align the horizontal or vertical myopic target by having the phone screen aligned with the darkest line lengthwise on the astigmatism target that you have identified as the spherical axis line, then switch to the horizontal myopic target for your reading. To make your reading start out far enough that the lines appear blurry, focus on the second line from the top and when the line start to get more clear as you move closer to the screen, begin a slow approach to the phone in small (1/8") increments, pausing ten seconds to allow your eye to relax, until you determine that one of the second line borders (top or bottom) has become in focus, (appears straight, and sharp over some parts of it and holds for ten seconds). For mild myopic measurements where you have to place the phone upright on the floor or a chair to obtain a blurry image so you can begin your measurement, you will be trying to obtain the furthest point away from the phone where the image appears to be in focus after a blink. Moving out a little bit more will cause the borders of the line to blur even after a blink, and sometimes it easier to use the outside lines on the target instead of the second from the top line used in closer measurements. Measure with a tape measure from the corner of your eye to the phones screen and record the measurement to the nearest 1/16" or centimeter. For vertical measurements, if your end point measurement is beyond 21" from the phones screen, your end point is likely to be on t1, from 20.90" to 12 1/16" on t2, from 12"-8.5" on t3, from 8.49"-6.42" on t4, and lower than 6.40" try t5. For horizontal measurements, if your end point measurements are beyond 20.75", your end point is likely to be on t1, from 20.70" to 13 1/16" on t2, from 13" to 8.5" on t3, 8.49 to 6.42 on t4, and lower than 6.40 try t5. By using these estimates and the general appearances discussion above, should direct you to the right thermometer containing your end point.

Out to in measurements have an adjustment needed for measurements of end points greater than −2.50 D, to obtain an estimate of your distance refractive error at that axis measured. If the end point is between −2.50 D and −2.60 D, just round up to −2.75 D. From 2.61 D to 2.84 D, just round up to the nearest +0.50 D (for example a −2.75 result would be rounded up to −3.25). Alternatively, for end points from −2.85 D to −3.25 D, just by dividing the endpoint in diopters by 0.80, will yield the same estimate (rounded off to the nearest 0.25 D). From end points from −3.26 D to −3.66 D, divide by 0.77. From end points from −3.70 D to −3.95 D, divide by 0.75. From end points from −4.00 D to −7.15 D, divide by 0.73. When dividing by 0.73, if your end point is with 0.05 D of the center between two 0.25 D options, just round UP (greater myopic value) to the nearest 0.25 D, all other measurements round off to the nearest 0.25 D. Beyond −7.32 D end point measurements estimates are not accurate.

T1 Measurements:

For vertical measurements on t1, the end point you are looking for is a very faint, thin white halo or line just inside the red line, sometimes accompanied by a faint grey blur running alongside it in the center of the segment. If the ten seconds of gazing at the white background space doesn't allow the white halos to emerge just inside the red lines which is often the case, then a ten second pull and release will allow you to see them if they are there. If you can identify the white halo just inside the red line, focusing on the red line as you move down the thermometer segment by segment, will often help the white halo to persist during your measurements as you try and identify the first segment where it disappears. During the pull part of the maneuver when you have maximally magnified the segments space, the white halo will often appear as a broader white space or halo bordered by a faint grey blurry line in the center of the space. On t1 during the ten second count it is helpful to focus on the grey blur just inside the white halo to help accentuate and define the white halo making it easier to follow when you release. You also can wait longer than ten seconds if it necessary, until you can clearly see the white space or halo prior to your release. In a hazy space segment, during the release part of the maneuver, the white halo will disappear and often the grey blur will merge into the homogeneous light grey center as well, where as a white space segment the white halo will persist as an often a barely detectable, but thin white halo (same brightness as the background white space), still just inside the red line, and the grey blurry line will merge with the grey blue blur off the blue line, just inside the blue line. Since the end point is pretty subtle at low refractive errors, performing the ten second pull and release maneuvers multiple times may be necessary for you to make your decision. If during your measurements the white halo clearly disappears, that segment is almost always a hazy space segment. Any part of the white halo that persist after the release identifies that segment as a white space segment no matter how thin it initially looks.

For horizontal measurements on the t1, the measurements are the same, using a ten second gaze to bring out the white halos just inside the red line, and confirming the individual segments with a ten second pull and release, until you have determined the first hazy space segment where the release part of the maneuver makes the white space disappear, and the first white space segment where after the release maneuver, a thin but detectable white halo or thin white line persist after the release.

T2 Measurements:

For end points on t2 often t4 thermometers look the same relatively well defined red and blue lines with a noticeable white halo equal in brightness to the white background space, most of the segments on the t1 target are grey across the whole segment. The upper segments on t1 and most of the segments on t2 may have a lighter grey white halo just inside the red line on vertical measurements, but the halos are duller than the white background space, and can easily be distinguished from white space segments by a ten second pull and release maneuver. Pulling the segments apart will create a real separation between the blurs, and a real white halo just as bright as the background white space (since that's what it is) and noticeably brighter than false halo which still exists but has moved just to the right of the new true white space or halo. With the release part of the maneuver the bright white space will disappear as the blur closes or snaps shut over the separation as the segment narrows, except in the white space segments where a thin white halo will persist and still match the brightness of the white background.

Again, for vertical measurements on t2 the white halos now are more easy to see as a white space or separation (with the background white space coming through) between the grey blur coming off the blue line bordered by a very faint vertical grey line at its edge towards the inside of the segment and the red line on the outside of it. The end point is where this separation ends, marking the first hazy space segment. On thinner thermometers and segments below one can still see a whitish grey space separating the blue and red lines, but when tested with a ten second pull and release allowing you to identify the true white separation or space (much brighter) just inside the red line, the release will always snap close over the space or cover the white space making it disappear with the release maneuver. Start with the larger thermometers and just follow the white halos down the thermometer which now appear as a white space separating the grey centers from the red line, located just inside the red line, usually you can just follow the halos down the segments, until the grey blur in the center finally moves all the way across to merge with the red line and the white space (equal in brightness to the background white space) is absent, defining that space as the first hazy space segment. There may still be a whitish grey space just inside the red line that's part of the grey blur but it will be noticeably duller than the white space in the segment just above it, and by performing a ten second pull and release maneuver at that segment you should notice as you release, while fixing your focus on the blue blur during the pull part of the maneuver, the blue blur will snap shut over the true white separation or space that you created by enlarging the segments center space on the pull part of the maneuver.

For horizontal measurements, it is more difficult because our eyes are train to accommodate on horizontal targets as we try and "read" them. To relax your accommodation just focus on the background white space for ten seconds, this will allow the white spaces separating the red and blue blurs to emerge, often the red and blue blurs may appear thinner a little bit as well. With your eye relaxed if you look at the whole t2 thermometer you can notice the white space separating the blue blur and the red line gets thinner as you move down the thermometer to thinner segments appearing to bevel upward towards the red line. When the separation disappears (the end of the central whitish grey space) you are usually at the first hazy space segment. This can be confirmed by a ten second pull and release maneuver remembering to focus on the blue line while counting and see if the blur closes over the entire white separation when you release the magnification, where it will persist on the segment just above it with the same maneuver defining that segment as the first white space segment. On the bottom five segments you are usually using true white halos as end points which can persist through a ten second pull and release, on the top five segments the end point is any white space (equal to the background white space in brightness) that separates the blue and red blurs that only emerges with your eye relaxed, brought out by ten second gaze at the background white space, or can be brought out and confirmed by ten second pull and release maneuvers.

If you are still unsure about the first hazy space segment, you can try a ten second pull and release, followed by 6 quick pull and release to see if the white space persists after the maneuvers, if it does count it as a white space segment. If the white space ever gets difficult to see just re-focus on the background white space for ten second to reset your focus without accommodation, and then continue your measurements.

Repeat your measurement if you get a different answer, continue the maneuvers until you get two outcomes the same. Again on larger thermometers after five segments on t2, instead of the true white space or halo that you are measuring on t1 thermometers, the end point is more of an any white space (equal to the brightness of the outside background white space) that persists as a separation between the blurs of the red and blue lines, and can hold through a ten second pull and release maneuver.

T3, T4 and T5 Measurements:

For horizontal measurements on some of the t3 and all of the t4, often after focusing on the white background space for ten seconds or more the white halos still might not emerge. If they still won't emerge maximally spread the widest segment apart on the thermometer you are measuring. This will allow you to identify the white halo just inside the red line or blur, now either focusing on the white halo and follow them down the thermometer or on the red blur which at times makes it easier for the white halos to maintain themselves, until you get to segments don't contain the white halos, or by now your end point is any white space separating the blue blur from the red line which appears to be the background white space coming through into the center of the segment. When you confirm the first white and hazy spaces by using a ten second pull and release, first on the suspected first hazy space segment noting the blur snap shut over the white halo (or the separation of the blurs allowing the white background space to come through) upon the release maneuver and not on the first white space segment where the white halo (although much narrower, and less defined) persist after the release maneuver. Remember to focus on the blue line or haze when you are counting to ten during the pull maneuver for easier measurements. Anytime you can close out a white halo with a ten second pull and release identifies that segment as a hazy space segment.

With vertical measurements on a t3 or t4 thermometer, the thermometer is usually very blurry from the high refractive error. Now you can approach the thermometer with the widest segment spread out with your fingers to maximally maximize the segment, while focusing on the white halo to increase the sharpness of the halo, if you get too close to the screen the white halo will merge with the white space between the blurs to disappear, too far out the grey blurs seem to envelope it. At the right distance from the phone where the maximum contrast between the white halo and the grey space to the right on vertical measurements exists, it is easier to make your measurements. Once the white space is maximized and staying at that distance from the phone, you can usually proceed immediately down the thermometer until you get to a segment where the white halo either disappears or gets much duller than the segment above it, and make your measurement, confirming the endpoint with a ten second pull and release and the persistence of the white halo at the first white space segment. Remember to focus on the blue line or blur when counting to ten while maximally spreading apart the segment, confirming the segment as a hazy space segment if the blue blur closes over the white halo, or as a white space segment if the white halo persist or immediately returns within few seconds of the release.

Use the same techniques for measuring on t5.

Scales for t Thermometers:

| Hyperopic - vertical measurements | |
|---|---|
| Results for spherical axis thermometer: (+.25(H), +.75(v)-+2.50) | T1 ___ White spaces; ___ hazy spaces |
| (+2.75-+3.75) | T2 ___ White spaces; ___ hazy spaces |
| (+4.00-+5.75) | T3 ___ White spaces; ___ hazy spaces |
| (+6.00-+6.75) | T4 ___ White spaces; ___ hazy spaces |
| (+7.00-+8.75) | T5 ___ White spaces; ___ hazy spaces |
| Results for astigmatism axis thermometers: (+.25(H), +.75(V)-+2.50) | T1___ White spaces; ___ hazy spaces |
| (+2.75-+3.75) | T2 ___ White spaces; ___ hazy spaces |
| (+4.00-+5.75) | T3. ___ White spaces; ___ hazy spaces |
| (+6.00-+6.75) | T4. ___ White spaces; ___ hazy spaces |

-continued

| Hyperopic - vertical measurements | |
|---|---|
| (+7.00-+8.75) | T5 ___ white spaces; ___ hazy spaces |
| Vertical measurements segments (−.25--1.75) | T1 ___ White space segments; or ___Hazy space |
| Horizontal measurements segments (−.25--2.00) | T1___ white space segments; or ___ Hazy space |
| Vertical measurements segments (−2.00--4.00) | T2___White space segments; or ___Hazy space |
| Horizontal measurements segments (−2.25--3.75) | T2___White space segments; or ___Hazy space |
| Vertical measurements segments (−4.25--6.25) | T3___White space segments; or ___Hazy space |
| Horizontal measurements segments (−4.00--6.25) | T3___White space segments; or ___Hazy space |
| Vertical and horizontal measurements segments (−6.50--8.75) | T4___White space segments; or ___Hazy space |
| Vertical and horizontal measurements segments (−9.00--10.50) | T4___White space segments; or ___Hazy space |

1. Hyperopic Thermometers (H1, H2, H3, H4)

Directions for Measuring H1 Through H4:

Vertical Measurements (for Axis within Thirty Degrees of Ninety Degrees):

Quick Directions:

At a reading distance of approximately 16", you will be asked to make two measurements. The first measurement will be the total number of completely grey segments (CGS), and the second measurement will be the total number of hazy space segments, which are defined as segments not containing true white spaces (which is a separation between the blur generated from the red line and the blue line, creating a white space just inside the blue line (for left eye measurements) and the red line (for right eye measurements) within the segment equal in brightness to the background whitespace, which need to be distinguished from secondary or false white spaces which are common in hazy space segments and occur at the same location (just inside the blue line for left eyes), but are duller (when compared to the background white space).

Directions for CGS Segments:

After a ten to twenty second gaze at the background white space to allow your eye to relax, starting with the bottom segment on h1, phone oriented along its up and down longitudinal axis, maximally magnified the image at rest) by spreading the image apart with your fingers (but don't hold the magnification) prior to reading the thermometers. First evaluate how many segments contain a central purple or grey central line or are completely grey segments defined by the absence of any white space inside the segment after a ten second pull and release. The white space need to be the same white spaces created by the pull portion that are retained after the release located in the same position. It is ok to re-test segments to confirm your answer, and you can ignore thin dull secondary white grey spaces just inside the blue line if when you release the grey appears to close all the way to the blue line, and the dull white space appears exactly the same on several segments below that segment. You can also ignore central white spaces on the other side of the segment if the segment also contains a central grey or purple line, and sometimes can occur in those segments. As soon as the secondary white space is wider than the segment below it, it is considered a central whitish space and doesn't count as a CGS, also if you wish you can spread the segment apart and confirm that the dull white space is replaced by a much brighter true white space at the same location in the segment's now magnified state.

Directions for Hazy Space Segment Measurements Along the Phones Widthwise Axis:

If only one segment is a completely grey segment, then measurements are made by first holding the phone vertically in your hands, then turning the phone sideways to flip the h1 thermometer along the phones widthwise axis, giving the thermometer a little more magnification making the measurements easier. Next place the phone on a flat surface, closing or patching the eye not being studied. With the h1 magnified along the width of the phone but measuring vertical axis, the true white space is detected by a ten second pull and release, followed by one quick pull and release immediately following for difficult reads to see if the white space can be made to close out, or whether the white space becomes more defined after the quick pull and release maneuver. Count as a white space segment if after the release there is retention of a faint, white, halo just inside the blue line, or a central grey line defining its outside border with the blur off the red line (absence of a grey line centrally usually indicated a hazy space segment). Throughout h1 and h4 measurements, if you can't tell for sure if there is a slight white halo, try an independent five quick pull and releases in a row just by themselves, a true white space will maintain itself, where a secondary or false white space will usually disappear before the fifth quick pull and release. You can repeat the five quick pull and release maneuvers, and this time while you are performing the maneuvers pay attention to the brightness of the white space inside the blue line before the pull portion, and see if with the pull portion the white space either becomes noticeably brighter or if no white space was present if a new bright white space appears in the segment during the magnified state only to disappear or become much duller in the contracted state. This verifies the presence of a secondary or false white space in a hazy space segment. In a white space segment, the white space present in both the contracted state and the magnified state although varying in width and size have similar amounts of brightness, and also won't disappear in the contracted state. Within the first 3 to 4 segments from the bottom, often the hazy space segments will appear to have a red hew or shade when viewing the center of the segments where the white space segments will appear to be whiter.

Directions for hazy space segments with the h1 oriented along its normal longitudinal (up and down) axis:

The most accurate method for determining the total number of hazy space segments is after you have done a careful CGS determination by determining the total CGS segments on h1 or h2, with a ten second pull and release, and the absence of a central whitish space, you will be directed to several segments on the h1 or h4 thermometer most likely to contain your end point the first hazy segment. By performing five quick pull and releases on these segments and noting which one of the segments are definitely white space segments where the brightness of the true white space as viewed in the upper right hand corner of the segment doesn't change through the maneuvers and is still present at the end of the maneuvers, as opposed to the first hazy space segment, the highest segment on the thermometer where the magnified state of the segment (pull portion) has a much brighter white space than the contracted state of the segment (segment after the release) and the white space is made to disappear during the maneuvers or if present changes into a much duller secondary white space when compared to the white background space. Count from the first hazy space down the thermometer to determine the total number of hazy space segments.

An Alternative Method for Estimating the End Point but Less Accurate:

From 2 CGS reading and above switch your method starting from the bottom up, to a ten second pull and release, followed by five quick pull and release maneuvers. This method will get you to a good estimate of your end point that is the segment identified as the first white space segment, and the segment immediately below that segment the suspected first hazy space segment. Because secondary white space are common, you must confirm the first hazy space segment by repeating the independent five quick pull and release maneuvers as discussed above to confirm the presence of a secondary or false white space; and the segment just above it (the suspected first white space) to confirm the continuity of the white space and equal brightness throughout the maneuvers. If this time the suspected first white space shows the characteristics of a hazy space segment instead (a brighter white space just inside the blue line replacing a duller white space as the segment is magnified), then move to the next segment above until the white space retains about the same amount of brightness as the segment is magnified, confirming the segment as the new first white space segment. Then count back from the new first hazy space segment to determine the total number of hazy space segments. Likewise if you recheck the first hazy space segment and you now believe the white space has about the same brightness with the maneuvers, count this space as a white space segment and move to the segment immediately below to try and find the first hazy space segment. At some point as you approach the upper segments on the thermometer it is more efficient to start at the top and work your way down the segments, using the exact same methods and directions as have already been discussed. On h4 measurements, we again start at the bottom and use the exact same methods for measurements, ten second pull and release, followed by five quick pull and release to get an estimate, and then confirm the first white space segment, and first hazy space segment with a separate quick five pull and release maneuvers as already discussed.

Detailed Instructions: (for Mixed Astigmatism)

Mixed Astigmatism Measurements:

In mixed astigmatism, (where one axis is nearsighted and the other is farsighted) for low refractive errors (towards the bottom of the thermometer), where the hazy segments begins (the widest segment where no central whitish space separating the blurs is apparent) is usually the first hazy segment; and where the central whitish spaces ends (the narrowest segment going from the top down that still contains a central white space) is usually the first white space segment on vertical measurements only. The first white segment can be confirmed by a prolonged (ten second) pull and release maneuver, having the segment spread open for ten seconds prior to release, allows the true white space or halo to noticeably linger at the end of closer, and close appreciably slower than the first hazy segment below.

Because in mixed astigmatism with low refractive errors there is a strong correlation between the last central whitish space segment also being the segment containing the last true white space as well; five multiple pull and releases often will cause the central whitish space to disappear as the blur becomes continuous over the whole segment allowing you to quickly identify the first hazy space segment. Or instead when you get to a segment that multiple pull and releases can't make the central whitish space disappear completely, count from the segment immediately below that space to the bottom of the thermometer to determine the total number of hazy segments for your measurement.

This is in contrast to if you have farsighted astigmatism or farsightedness, or mixed astigmatism with higher refractive errors (towards the top of the thermometer) your end point is when the true white space persists through five multiple pull and releases, allowing you to maintain your fixation and focus on the bright white space even though it may thin dramatically, it can still persist at the end of the contractions on some of the maneuvers usually in the presence of the central whitish space, below the central whitish space can close over the true white space identifying those segments still as hazy space segments, and the grey blur can close over it in still narrower segments.

Horizontal Measurements:

General Information and Descriptions:

Smartphone measurements for horizontal lines within sixty degrees of the 180 axis (horizontal line): This time your end point will be the same throughout all your measurements, the presence or absence of a thin bright, white line or space or halo just below the blue line (blue line always on top, red line at the bottom for horizontal measurements). The true white space you are measuring is an actual space between the blur of the red line and the blur of the blue line, it is just the white background space of the screen coming through if the blurs don't actually touch or merge. As you move up the thermometer from the narrowest segments where no white space may be seen, or even a dark grey or purple line in the center as the two blurs overlap, it is easy to count these segments as a hazy segment. Eventually a central whitish light grey space will emerge between the blurs as the overlap becomes less complete, as soon as you notice this first lighter space developing between the red and blue line blurs, use your fingers to spread the distance between the lines, or maximally magnify the image to recognize the true white space that will appear as a bright white space, just inside the blue line, bordered on the bottom by the central whitish space, because there is no overlap of the blurs, just the background white screen. Using this spread and release technique at this segment the blurs will quickly snap close over the separation or the white space you are measuring as soon as you release the magnification. The central whitish space, a white-light grey area will still persist between the two blurry lines after the release has finished contracting, and often a secondary whitish grey halo will also immediately appear just inside the blue line, but the actual bright true white space or true separation between the blurs will disappear as the blurs snap shut over the separation. It is important to distinguish the true white space form the secondary white space both which appear at the same location just inside the blue line. The secondary white space will always appear greyer when compared to the background white space outside the segment, where as a true white space persisting after the contraction will be the same shade of white and just as bright as the background white space (since that what it is) it will appear as an extension of the background white space into the edge of the segment. If you are not sure between the two you can re-spread the segment a true white space may get wider or appear to move up a little, but will not change its appearance and will be the same brightness, a secondary white space will immediately get replaced by a much brighter true white space.

Quick Directions:

At the same distance from the phone (approximately 16") with the phone oriented along either the astigmatism axis line (first darkest line on the astigmatism target encounter moving out to in) or the spherical axis line (second darkest line on the astigmatism target encountered moving out to in). Use only h3, and h4 to measure horizontal lines.

To begin with, determine the total number of completely grey segments (CGS). Go to the bottom or the thinnest segment on h3 and measure just as if you were measuring for a vertical CGS; perform one ten second pull and release, moving up the thermometer (towards the left wider segments), segment by segment, until after focusing on the white space just beneath the blue line created by the magnification induced by the ten second pull portion of the maneuver, there is a central whitish space that persists, appearing just underneath the blue line, after the release portion of the maneuver, or if the red blur appears to close all the way to the blue line, but there appears to be a widening of the secondary white space compared to the secondary white spaces to the right on narrower segments, then that segment also doesn't count as a CGS segment. Count the number of segments below that segment where the central whitish space first persists, or the secondary white space appears wider than the rest to determine the total number of CGS segments.

Next, if the CGS measurement is six CGS or more, your end point is likely to be on h4, start at the narrowest segment on h4 performing a ten second pull and release maneuver followed immediately by a quick pull and release, to see if you can get the grey blur close all the way to the blue line closing out the white space under the blue line, identifying the segment as a hazy space segment. When performing the "pull portion" of the maneuver, on the h4 thermometer you have to hold the segment apart, waiting for your eyes to see the white space as a clearly defined, bright white space with sharp borders. It will sometimes take longer than ten seconds, but if you continue to focus on the grey center of the segment eventually your eyes will relax allowing to focus on the white space without making it immediately disappear, finally allowing you to suddenly release the magnification and with the release determine the effect on the white space after your second quick pull and release. When you get to a segment where the white space persists through the one, two punch, you have just estimated the location of the first white space segment. Next confirm the first white space and hazy space segments by performing the independent five pull and release maneuvers, comparing the relative brightness of the white spaces just under the blue line, in their "magnified" state to their "released" state, to confirm the presence of a secondary white space on the first hazy space segment, or the presence of a true white space on the first white space segment. On the first white space segment the white space will appear continuous and similar in brightness throughout the maneuvers becoming much more obvious and wider in the magnified state, but although very thin will usually persist in the released state at the same level of brightness. On the first hazy space segment there will be a clear difference in the level of brightness of the white space just under the blue line between the two states. On most h4 segments the white space will completely disappear after the release portion usually before the end of the five quick pull and releases, in the first hazy space segment making the reading easier to obtain. Also since it is necessary to see the white space under the blue line to make your measurements, when you are making your independent five quick pull and releases, on higher refractive errors you need to hold or pause the first "pull portion" or magnification long enough to obtain a clearly defined white space to allow you to make your comparisons, the remaining 4 pull and releases occur at normal slow but consecutive speed. Again, most often with h4 measurements when performing the independent five quick pull and releases the white space completely disappears after the release portion on the first hazy space segment, but just remain barely visible on the first white space segment.

If the CGS measurement is five CGS or less, then starting with the top widest segment on h3 and working your way downward toward narrower segments, segment by segment, performing two consecutive ten second pull and release maneuvers to try and close out the white space just under the blue line. During the first ten second pull and release maneuver, while counting off the ten seconds (or more if necessary) you are focusing on the grey blur just below where you expect the white space to appear to help it become well defined and bright so you can make your measurement. Once it is established quickly release the segments, but when you re-spread the segments for your second ten second pull and release maneuver you should just be focusing on the white space the entire time, and through the release, to see if it disappears or persists. When it does finally disappear after the maneuvers, this will allow you to estimate the first hazy space segment on h3, which again needs to be confirmed by using the independent five quick pull and release maneuvers to identify the first hazy space segment and the first white space segment as discussed above. With very small refractive errors it may be difficult to identify the true white spaces under the blue line because the grey blur off the red line is so faint it won't have that faint grey line that usually defines it inside border. Instead it will appear as a white glow off the blue line but it follows all the same rules and methods, and will become more apparent as the segments get narrower further down the thermometer.

Detailed Instructions: (Optional)

When measuring for mixed astigmatism (where your spherical axis line is nearsighted and your astigmatism axis line is farsighted); start at the narrowest segment on the thermometer and after you have pause to gaze at the thermometer for fifteen to twenty seconds to allow your eye to relax, just count up the segments that are hazy all the way across, until you get to a segment that you can barely first detect a central whitish space between the blurs appear. Most often this is your first white space segment, but you can confirm by using the pull and release maneuver, holding the segment (suspected white space segment) spread apart for ten seconds and then releasing to note if the white space or a halo persists along the outside edge as it closes, or with five spread and release maneuvers with five seconds in between at least on some of the releases incomplete closure at the end of the contractions. With mixed astigmatism this is all you need to confirm a white space segment since the presence of any central white space is often an accurate end point instead of the presence of a true white separation or space for all the other horizontal farsighted measurements.

Count from your first hazy space back down the thermometer to obtain the total number of hazy space segments and record your answer, after repeating your measurements until you get the same answer or end point more than once.

At times it is easier to use the analogy of thinking of the segment as a window with a grey shade over it, that closes from the bottom up. By pulling or spreading the window open more (the ten second initial pull), you can see the white sky peeking underneath the grey shade at the top or edge of the shade, which matches the white sky above outside the segment. You can identify the white space segments by noticing after you release the shade the white sky is still peeking underneath the end of the shade as if it did not close completely, where as the hazy space segment the shade appears to have completely closed. Once you have identified the first hazy space segment, repeat the five pull and release maneuvers to confirm you get the same outcome. (You get five more tries to close the shade completely)

Myopic Measurements

Myopic horizontal and vertical targets, for both spherical and astigmatism axis line measurements: (all clients with nearsighted refractive error)

General Instructions:

Start out far enough from the target that it is still blurry.

If your spherical axis line or astigmatism axis line to be measured is horizontal, focus on the target that contains long horizontal lines after you have rotated the phone so that the myopic target is aligned with your spherical or astigmatism axis line to be measured. Focus on the second horizontal black line from the top towards the left outside fence post (or the vertical line along the outside edge of the horizontal lines).

If your spherical axis line or astigmatism axis line to be measured is a vertical line (within thirty degrees of a straight up and down line), focus on the second vertical line from the left just below the top hash mark (horizontal line along the top border of the vertical lines).

Instructions for Out to in Measurements:

Out to in Measurements for Estimating Myopic Refractive Errors and Correct t-Thermometers Containing End Points:

To begin with use the horizontal myopic target or vertical myopic target aligned with the spherical axis line and/or the astigmatism axis line you have identified on the astigmatism target above (align the horizontal or vertical myopic target by having the phone screen aligned with the darkest line lengthwise on the astigmatism target that you have identified as the spherical axis line, then switch to the horizontal myopic target for your reading. To make your reading start out far enough that the lines appear blurry, focus on the second line from the top and when the line start to get more clear as you move closer to the screen, begin a slow approach to the phone in small (⅛") increments, pausing ten seconds to allow your eye to relax, until you determine that one of the second line borders (top or bottom) has become in focus, (appears straight, and sharp over some parts of it and holds for ten seconds). For mild myopic measurements where you have to place the phone upright on the floor or a chair to obtain a blurry image so you can begin your measurement, you will be trying to obtain the furthest point away from the phone where the image appears to be in focus after a blink. Moving out a little bit more will cause the borders of the line to blur even after a blink, and sometimes it easier to use the outside lines on the target instead of the second from the top line used in closer measurements. Measure with a tape measure from the corner of your eye to the phones screen and record the measurement to the nearest 1/16" or centimeter. For vertical measurements, if your end point measurement is beyond 21" from the phones screen, your end point is likely to be on t1, from 20.90" to 12 1/16" on t2, from 12"-8.5" on t3, from 8.49"-6.42" on t4, and lower than 6.40" try t5. For horizontal measurements, if your end point measurements are beyond 20.75", your end point is likely to be on t1, from 20.70" to 13 1/16" on t2, from 13" to 8.5" on t3, 8.49 to 6.42 on t4, and lower than 6.40 try t5. By using these estimates and the general appearances discussion above, should direct you to the right thermometer containing your end point.

Out to in measurements have an adjustment needed for measurements of end points greater than −2.50 D, to obtain an estimate of your distance refractive error at that axis measured. If the end point is between −2.50 D and −2.60 D, just round up to −2.75 D. If the (end point (D)+2.25 D<−0.85 D), just add the result of the (end point (D)+2.25) to the end point (D) (round off to the nearest 0.25 D) for an estimate of your distance refractive error at that axis measured. For example, end point −3.01, −3.01+2.25=−.76, −3.01−0.76=−3.77, −3.75 is your estimated refractive error at that axis at distance. This adjustment method works up to end points of −3.10 D. Alternatively, for end points from −2.85 D to −3.25 D, just by dividing the endpoint in diopters by 0.80, will yield the same estimate (rounded off to the nearest 0.25 D). From end points from −3.26 D to −3.66 D, divide by 0.77. From end points from −3.70 D to −3.95 D, divide by 0.75. From end points from −4.00 D to −7.15 D, divide by 0.73. When dividing by 0.73, if your end point is with 0.05 D of the center between two 0.25 D options, just round UP (greater myopic value) to the nearest 0.25 D, all other measurements round off to the nearest 0.25 D. Beyond −7.32 D end point measurements estimates are not accurate.

Following obtaining the refractive power estimates for both your spherical and astigmatism axis lines, next proceed the t thermometer directions for myopic refractive error determinations and proceed to the specific thermometer you have been directed to by your estimates.

Optional Measurements Utilizing the Astigmatism Target: (Only for Clients Over Forty Years Old)

Starting very close to the screen while viewing the astigmatism axis or spherical axis line you are measuring for refractive power, the line should appear as a wide blurry light grey image, sometimes with a darker border on one of its sides. As you move slowly out in small increments, you will usually notice a thin dark line emerge from the center of the blurry, light grey, linear image. As you continue moving outward you may notice the sides of the blurry image forming thin dark lines, if the central thin line is still present you may have three distinct lines noticeable. Again as you continue to move outward the center line will merge into the background space within the borders, to form a soft light grey line. Eventually after an incremental movement outward the light grey line will all of a sudden appear darker, sometimes just preceded, with just one margin turning darker just before the whole line becomes darker. We will be asking you to recognize these characteristic during your measurements and the closest point to the screen that they occur can help give us a good starting estimate for your refractive power along the axis line you are measuring.

First you will determine your end of the line (EOTL) end point, which will determine which of the typical characteristic features of the blurry line's progression from a light grey blurry image to a dark grey continuous single line you will be using to determine your end point for making a measurement to predict the refractive power of your eye along that axis. If the (EOTL) measurement is less than ten inches away from the screen, place your phone, vertically aligned (up and down) and positioned along the spherical or astigmatism axis line you are measuring, on a desk or table to make your measurement; if it is more than ten inches away use a chair to place your phone on. Bending too far forward from your waist to make your measurements can affect the accuracy of your measurements.

Instructions for (EOTL) Measurements:

When measuring vertical lines on the astigmatism target on smartphone, start out far enough that the vertical line is blurry move towards the astigmatism target until the last point closest to the screen where the vertical line maintains itself as a single continuous, dark line, where a small movement forward causes the line to dramatically thin, get lighter, or blur, most of the time double (a lighter thin line along one of its borders) or separate into multiple thin lines. Beyond 11" the (EOTL) is identified by the dark grey line suddenly (with one slight movement forward) becoming light grey. This is the end of the line, (EOTL) end point. Measure from the corner of your eye to the phone screen, measure for both spherical axis line and astigmatism axis line (both vertical and horizontal axis for 2a). Confirm the measurements by obtaining two measurements less than 1/8" apart.

If this (EOTL) end point is 6 3/16" or less from the screen your end point is achieved by starting close enough to the phone screen that the vertical line is completely blurry. Now slowly move out in small increments blinking with each movement, until at least two vertical thin dark lines form, they usually define the outside borders of the light grey line, but may occur inside the vertical blur (sometimes three lines will form), they need to be equal in definition as lines. When this first happens (closest to the phone screen that this occurs) make your measurement.

If your (EOTL) end point is from 6 3/16" to 6.25", first time the light grey line has one of its margins become dark.

If your (EOTL) original end point is from 6.25" to 6 5/8", your measured end point is the closest point to the screen where the central dark thin line first merges into the side blur and becomes indistinguishable, as a light grey line.

If your (EOTL) original end point is from 7" to 9 3/8", your end point (measuring in to out) is when a small movement outward is associated with the light grey line suddenly becoming darker, by moving forward slightly the line appears dramatically lighter, slightly outward makes it dramatically darker in appearance. For large refractive errors this also almost at the same distance as your (EOTL), and corresponds to the closest point where a single dark line is formed, where a small movement forward causes the line to breakdown or begin to double, or form a outside double image.

If it is from 9 3/8" and out, use an out to in measurement, start where the vertical line is blurry move in noticing with each small incremental movement forward the vertical line grows or gets longer, until the small movement forward causes the line to shorten or shrink two times in a row, go back to the longest line position and make your measurement.

Horizontal Line Measurements:

Measuring horizontal spherical and astigmatism axis estimates using an astigmatism target: (again shorter measurements (high refractive errors) use a table or desk so you don't have to bend at the waist to make your close measurements) Start by identifying the (EOTL) end point as defined above for the horizontal axis line to be measured (the distance closest to the phone screen where the horizontal lines maintains itself through several seconds of gazing, where making one more small movement forward causes a faint double line to appear along the line, or causes the line to become a lighter, wider, grey blurry linear image or out of focus. The original astigmatism target can be expanded by rotating the phone ninety degrees so the image is viewed width wise if it's easier.

If the (EOTL) measurement comes in 5 7/8" or closer use an in to out, starting close enough to the phone that horizontal line is blurry make small incremental movements outward until you can first identify two distinct, equally defined lines, lines that can hold for ten seconds. If the lines aren't detected repeat the measurement blinking often to allow your eye to reset its focus sometimes allowing the lines to emerge. Make your measurements at this point.

For (EOTL) measurements from 6" to 7 3/8" your end point is a soft grey line which occurs while moving closer to the screen after you gone through the obvious dark grey lines in focus (out to in), and where one more small movement towards the image causes the image to form a faint double line just above or below part of the line, or at times a dramatic change to a blurry much wider, lighter grey out of focus image.

From 7 3/8" and out, your end point while moving out to in, starting where the horizontal line is clearly out of focus, is the widest dark line, often most easily identified by once the line is dark and in focus, follow where the line intersects with the outside circle noting after each small movement forward if the circle appears to expand or contract, (the line appears to grow or shrink). When the line is at its first longest point, once the line is in focus, as you move in, it is also at its widest. At the end point the line should maintain it clear focus and not thin or fade over twenty seconds.

Spherical axis power estimate _" or _ diopters;
Astigmatism axis power estimate _" or _ diopters.
Once estimates have been obtained from the astigmatism axis targets, they can be confirmed by obtaining measurements on specific myopic thermometers:

| Astigmatism target end points | Myopic thermometers |
|---|---|
| −.25−−1.75 diopters | Use t1 for vertical measurements |
| −.25−−2.00 diopters | Use t1 for horizontal measurements, |
| −2.00−−4.00 diopters | Use t2 for vertical measurements. |
| −2.25−−3.75 diopters | Use t2 for horizontal measurements. |
| −4.25−−6.25 diopters | Use t3 for horizontal and vertical measurements. |
| −6.50−−8.75 diopters | Use t4 for vertical and horizontal measurements. |
| −9.00-10.50 diopters | Use t5 for vertical and horizontal measurements. |

Out to in Measurements for Predicting Refractive Errors Based on Specific End Points:

For clients 40 years old and younger, out to in measurements are the best method for determining your refractive error power.

For clients 40 years old and older, if your astigmatism target estimated either your spherical axis line or astigmatism axis line to be −3.50 to −1.00 you can use out to in measurements. For (EOTL) estimates −2.00 and below you might want to begin your measurements from a standing position with the phone on a table or a chair to be able to start with a blurry image.

Below −1.00 measurement is easier to use the t−1 or H1 (widthwise) thermometer, for vertical measurements, or the H3 (widthwise) thermometer for horizontal measurements and adjust for age if you are forty years old or older when measuring on a phone screen. People younger than forty can try maximally magnifying the myopic horizontal or vertical target and place the phone on its side upright to attempt to measure at a greater distance to the phone.

Again starting out far enough from the screen that the image is blurry, slowly by moving out to in, towards the screen, in small 1/8 inch incremental movements, the lines will begin to be more focused and appear closure to you. The end point always has a sharply focused line, so quickly make your incremental movements inward waiting just a few seconds in between movements to refocus and determine that the image appears closure to you with the small movement forward. Once the image appears more focused you need to count to ten under your breath between your incremental movements forward, to allow your eye to relax its focus between movements. Keep moving closer as long as the line appears to be moving closer to you, at some point the line will appear to push out a little bit or appear to move further from you, make one more slight movement forward to confirm that the line appears to move further away, then move incrementally backwards to confirm that the line appears to move toward you even though you are actually moving away from it. Make one more movement back until the target appears to move away from you, then move forward and measure that end point which is the point closest to the target that a small movement forward will make the target appear to move away from you. You can measure this end point using a tape measure as described above (with your fourth finger placed over the face of tape measure just touching the boney ridge at the outside corner of your eye, with the side of the tape measure flush up against the side of your temple), so you are measuring actually from the front of your orbital rim to the target on your phone. Enter your measurement in inches or centimeters below. If the line always appears to move closer to you and never appears to push away from you, then your next best end point is when the line first becomes in sharp focus and doesn't thin or want to fade as you continue to focus on it for twenty seconds.

For clients with both spherical axis lines and astigmatism axis lines less than −3.50: Now go to the adjacent myopic target on the same screen page to obtain your other axis line measurement. You will be using the same technique as above to determine the distance at which a small forward movement appears to make the visual target move further away. If the myopic target you are using has long vertical lines, fix your gaze to the second vertical line from the left, viewing it near the top, close to the top hash mark. If the long lines are horizontal, look at the second line from the top, close to the left fence post, or vertical line at the border. Again start out far enough away from your phone, that the target is blurry, gradually approach the target until the white lines separating the vertical black lines become as bright as the background, continue moving forward making a decision after each small movement whether the image is appears to be closure or further away from your last position (the white spaces around the vertical black line should not be enlarging and the black lines should not be getting more blurry after each movement forward, if they are, you are too close to the target and need to restart further away and approach again). Once a small movement forwards appears to make the target appear further away, reconfirm by making one more small movement forward, and then move backwards in small steps to confirm the image appears to move closure to you, until it appears to move further away again, move forward again one step and make your measurement, by measuring with the tape measure from your orbital rim to the phone and record your finding below.

Instructions for in to Out Measurements:

For clients over forty years old, blurry vision at near finally gives you an advantage. If your astigmatism target estimates for either your spherical axis line or astigmatism axis line was equal to or greater than −3.75 its best to use and in to out approach. The phone should be placed on a table or desk in front of you again with the phone position oriented or aligned with the spherical or astigmatism axis line that you are measuring. Avoid placing the phone on a low table or a chair which will cause you to bend at the waist to make your measurements for these nearer measurements. This can lead to less accurate measurements.

Begin by starting close enough to the screen that the line appears thinner and out of focus; and by noticing that, the line after appearing further away with an initial small movement outward, may appear to move a little bit closer to you, and slowly expand as you continue to focus on the line over the next few seconds (your eye is relaxing accommodation as it refocus on the line). It is almost as if the line is following you outward as you make small movements away from the screen. By noting and stating "closure or further" or "following" or "stays away" after evaluating each small movement outward for a few seconds, until you get TWO "furthers" in a row, (where the line doesn't appear to move at all, or stays further away) then making two small movements closure back to your end point (the line should appear to be getting closure with each movement back) where one more movement towards the screen will again make the line appear to move further away again, can help define your end point (the distance from the computer where a small movement towards or away from the screen appears to make the line move further away).

The end point can be confirmed with a small movement forward, causing the line to get thinner or appear a little further away; if instead, the line appears to get closer to you and stays in sharp focus move in closure again until it appears to thin, or the line appears to move slightly away from you. At the end point a small movement away from the screen, makes the line thinner, but stays in sharp focus; sometimes just no change occurs but the line appears to move further away from you. A small movement towards the screen initially makes the image appear to move further away, and narrow. Return to the end point position, where the line appears at either at its widest and closest, and measure from the corner of your eye to the computer screen.

If you have difficulty telling if it is closer to you after each movement outward you can use the following method. With measurements for spherical and astigmatism axis lines, you may also measure from in to out, starting close enough to the computer screen that the longer lines on the target are blurry and thin. Keep moving out in tiny increments (⅛") noting whether longer line gets wider or thicker with each movement outward. Wait a ten seconds between the movements outward, and state to yourself "wider or thinner" after each movement. Your end point measurement is when the line is at its widest, the line often becomes in focus long before your end point arrives, and you must get two "thinners" in a row before you stop moving outward. Make two small movements inward to get back to your end point, where a small movement closure towards, or further away from the computer both will make the line appear thinner.

Required Re-Measurements for High Myopic Refractive Errors (Alternative Method):

On your vertical myopic target measurements above −7.25 (5¼" or less from the screen on your end point measurement) up to −9.0 (4.375" from the screen and nearer); or for (EOTL) measurements closure than 6⅛", or vertical axis measurements −8.00 or greater on the astigmatism target measurements; you need to re-measure your end point. This time while moving in to out, your end point is the first time the blurry second black line from the left, forms a sharp, focused, straight border on ONE of its sides after ten seconds of gaze. (OK for the border to have bumps). Use this end point distance from the screen as your final measurement. Above −9.00 (as measured on your astigmatism target estimates) this method is less accurate, the end point becomes when ANY PART of the white space inside the black lines, by moving in to out, first has the same whiteness as the background white space on the screen.

Spherical axis line (line in focus closest to the screen) _",
Astigmatism axis line (line in focus furthest from the screen) _"

Figure 16:
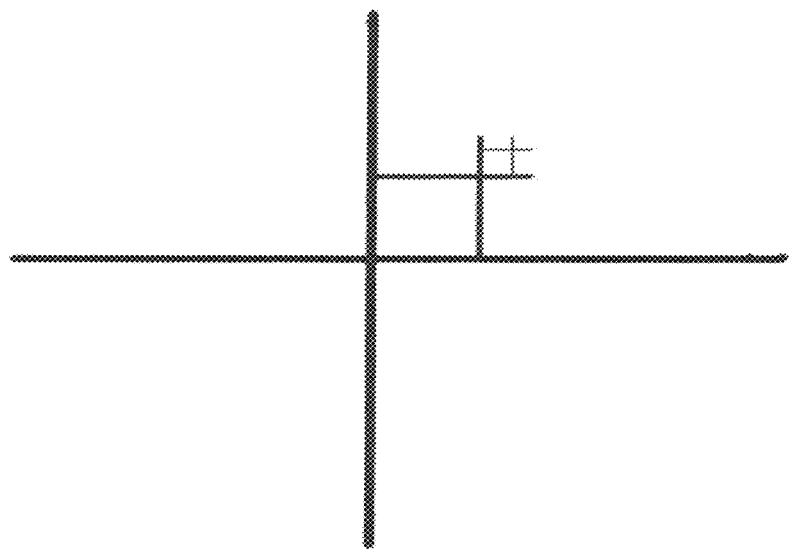
FIG. 16 illustrates an exemplary inflexion point target according to an embodiment.

Instructions for Inflexion Point Target:

Place the phone flat on a table or desk, aligned with either axis. While viewing the smallest lines on the inflexion point target (e.g., as illustrated in FIG. 16), slowly move forward towards the phone noting that the spherical axis line becomes darker and moves or shifts in front of the astigmatism axis line. Next move slowly out until the astigmatism axis line becomes darker and shifts in front of the spherical axis line. Keep moving back and forth shifting your direction of movement when the opposite line shifts in dominance (begins to get darker than the other line) to narrow the range or distance between the when the lines shift in dominance to obtain the center position where the lines are equal in dominance or continuously shift back and forth without changing your distance from the screen. Make your measurement from this middle position, where both lines are equal in darkness, or where a tiny movement in either direction makes the opposite line darker. If the small lines are difficult to see from being too blurry or double to assess which one is darker (large astigmatism), then use medium lines on the inflexion point target. The inflexion point determinations are accurate for vertical and horizontal spherical axis lines from −5.00 and less refractive error, (may need to use medium lines above 4.50 diopters of astigmatism power for more accurate results). Inflexion points are rounded up to the nearest 0.25 diopter. For spherical axis lines −5.00 and above, inflexion points can still be accurate but need to be adjusted based on their relative spherical power and the astigmatism power. Make multiple measurements until two measurements are in agreement or confirmed (less than ⅛" apart).

What is claimed is:

1. A method comprising:
   displaying a line pattern to a user, the line pattern including a first line and a second line;
   ascertaining a distance between the line pattern and the user;
   varying an aspect of the line pattern, the aspect being at least one of a width between the first line and the second line, a thickness of the first line or the second line, a darkness of the first line or the second line, or a color of the first line or the second line; and
   quantifying a refractive error of the user based on the distance and a selected variance of the line pattern, the selected variance corresponding to a particular aspect variance of the line pattern identified by the user, and the quantifying further comprising accessing a lookup table, wherein the lookup table associates a particular refractive error value to each of a plurality of line pattern aspect combinations.

2. The method according to claim 1, the quantifying comprising quantifying at least one of a myopic refractive error or a hyperopic refractive error.

3. The method according to claim 1, the quantifying comprising quantifying at least one of a myopic astigmatism refractive error or a hyperopic astigmatism refractive error.

4. The method according to claim 3, the displaying further comprising displaying an astigmatism target, the quantifying of the at least one of the myopic astigmatism refractive error or the hyperopic astigmatism refractive error further comprising determining an astigmatism axis.

5. The method according to claim 4, the astigmatism target including an astigmatism axis wheel comprising a plurality of arc lines, the determining of the astigmatism axis based on a particular arc line selected by the user.

6. The method according to claim 3, the quantifying comprising quantifying a mixed astigmatism refractive error.

7. A non-transitory computer-readable storage medium, comprising:
   a memory component configured to store computer-readable instructions, the computer-readable instructions including instructions for performing the following acts:
      displaying a line pattern to a user, the line pattern including a first line and a second line;
      varying an aspect of the line pattern, the aspect being at least one of a width between the first line and the second line, a thickness of the first line or the second line, a darkness of the first line or the second line, or a color of the first line or the second line;
      receiving an input corresponding to a focused line pattern variance selected by the user, the input identifying a particular line pattern aspect combination associated with the focused line pattern variance; and
      quantifying a refractive error of the user based on the input and an approximate distance between the line pattern and the user, the quantifying further comprising accessing a lookup table, wherein the lookup table associates a particular refractive error value to each of a plurality of line pattern aspect combinations.

8. The non-transitory computer-readable storage medium of claim 7, the input further comprising an image of the user contemporaneous to the displaying, the quantifying further comprising extrapolating the approximate distance from the image.

9. The non-transitory computer-readable storage medium of claim 8, the extrapolating comprising extrapolating the approximate distance based on an approximate arm length.

10. The non-transitory computer-readable storage medium of claim 8, the extrapolating comprising comparing the image to a reference image of the user.

11. The non-transitory computer-readable storage medium of claim 8, the extrapolating comprising extrapolating the approximate distance based on measured dimensions of a reference object within the image.

12. The non-transitory computer-readable storage medium of claim 7, the varying controlled via a user calibration of the line pattern.

13. The non-transitory computer-readable storage medium of claim 7, the displaying further comprising displaying an astigmatism target, the quantifying further comprising determining an astigmatism axis.

14. The non-transitory computer-readable storage medium of claim 13, the astigmatism target including an astigmatism axis wheel comprising a plurality of arc lines, the determining of the astigmatism axis based on a particular arc line selected by the user.

15. The non-transitory computer-readable storage medium of claim 13, the determining of the astigmatism axis based on compass data received from a user device.

16. A method comprising:
   receiving user data associated with a viewing of a line pattern comprising a first line and a second line, the user data identifying parameters associated with the line pattern and a distance between the line pattern and a user, the parameters including at least one of a width between the first line and the second line, a thickness of the first line or the second line, a darkness of the first line or the second line, or a color of the first line or the second line; and determining a refractive error of the user based on the parameters associated with the line pattern and the distance between the line pattern and the user, the determining comprising accessing a lookup table, wherein the lookup table associates a particular refractive error value to each of a plurality of line pattern parameter combinations.

17. The method of claim 16, the user data further comprising data identifying an astigmatism axis, the determining comprising determining an astigmatism refractive error based on the astigmatism axis.

* * * * *